United States Patent
Gruber et al.

(10) Patent No.: US 6,326,458 B1
(45) Date of Patent: Dec. 4, 2001

(54) CONTINUOUS PROCESS FOR THE MANUFACTURE OF LACTIDE AND LACTIDE POLYMERS

(75) Inventors: Patrick Richard Gruber, St. Paul; Eric Stanley Hall, Crystal; Jeffrey John Kolstad, Wayzata; Matthew Lee Iwen, Richfield; Richard Douglas Benson, Long Lake; Ronald Leo Borchardt, Eden Prairie, all of MN (US)

(73) Assignee: Cargill, Inc., Minneapolis, MN (US)

( * ) Notice: Subject to any disclaimer, the term of this patent is extended or adjusted under 35 U.S.C. 154(b) by 0 days.

(21) Appl. No.: 08/133,445

(22) Filed: Oct. 7, 1993

Related U.S. Application Data

(63) Continuation-in-part of application No. 07/935,059, filed on Aug. 24, 1992, now Pat. No. 5,247,073, which is a continuation-in-part of application No. 07/825,059, filed on Jan. 24, 1992, now Pat. No. 5,142,023.

(51) Int. Cl.[7] .......................... C08G 63/08; C08G 63/82; C08G 63/91; C07D 319/12

(52) U.S. Cl. ............................ 528/354; 525/415; 526/68; 528/357; 528/361; 549/274

(58) Field of Search .................................. 528/354, 357, 528/361; 525/415; 526/67, 68; 549/274

(56) References Cited

U.S. PATENT DOCUMENTS

| | | | |
|---|---|---|---|
| 1,095,205 | 5/1914 | Gräter et al. | 528/361 |
| 1,849,107 | 3/1932 | Moss | 528/354 |
| 1,995,970 | 3/1935 | Dorough | 528/354 |
| 2,396,994 | 3/1946 | Filachione et al. | 528/354 |
| 2,703,316 | 3/1955 | Schneider | 528/357 |
| 2,758,987 | 8/1956 | Salzberg | 528/354 |
| 2,951,828 | 9/1960 | Zeile et al. | 528/354 |
| 3,268,487 | 8/1966 | Klootwijk | 528/357 |
| 3,322,791 | 5/1967 | Selman | 549/274 |
| 3,531,561 | 9/1970 | Trehu | 264/210 |

(List continued on next page.)

FOREIGN PATENT DOCUMENTS

| | | |
|---|---|---|
| 808731 | 3/1969 | (CA) . |
| 863673 | 2/1971 | (CA) . |
| 923245 | 3/1973 | (CA) . |

(List continued on next page.)

OTHER PUBLICATIONS

W. Carothers, G. Dorough, and F. Van Natta ("Studies of Polymerization and Ring Formation. X. The Reversible Polymerization of Six–Membered Cyclic Esters", Jan. 1932, *American Chemical Society Journal,* v. 54, pp. 761–772).

E. Filachione, E. Costello, T. Dietz and C. Fisher, ("Lactic Acid Derivatives as Plasticizers Esters of Polymeric Lactic Acid", Jul. 1951, *Bur. Agric. Ind. Chem.,* v. 11, pp. 1–11).

D. Deane and E. Hammond ("Coagulation of Milk for Cheese–Making by Ester Hydrolysis", Jun. 1960, *Journal of Dairy Science,* v. 43, pp. 1421–1429).

(List continued on next page.)

*Primary Examiner*—Shelley A. Dodson
(74) *Attorney, Agent, or Firm*—Merchant, Gould, Smith, Edell, Welter & Schmidt, P.A.

(57) ABSTRACT

A process for the continuous production of substantially purified lactide and lactide polymers from lactic acid or an ester of lactic acid including the steps of forming crude polylactic acid, preferably in the presence of a catalyst means in the case of the ester of lactic acid, to form a condensation reaction by-product and polylactic acid, and depolymerizing the polylactic acid in a lactide reactor to form crude lactide, followed by subsequent purification of the crude lactide in a distillation system. A purified lactide is then polymerized to form lactide polymers.

17 Claims, 6 Drawing Sheets

U.S. PATENT DOCUMENTS

| | | | |
|---|---|---|---|
| 3,636,956 | 1/1972 | Schneider | 128/335.5 |
| 3,772,420 | 11/1973 | Glick et al. | 264/102 |
| 3,773,919 | 11/1973 | Boswell et al. | 424/19 |
| 3,839,297 | 10/1974 | Wassermann et al. | 260/78.3 |
| 3,887,699 | 6/1975 | Yolles | 424/19 |
| 3,912,692 | 10/1975 | Casey et al. | 528/354 |
| 4,045,418 | 8/1977 | Sinclair | 260/78.3 |
| 4,249,531 | 2/1981 | Heller et al. | 128/260 |
| 4,273,920 | 6/1981 | Nevin | 528/361 |
| 4,279,249 | 7/1981 | Vert et al. | 128/92 |
| 4,595,713 | 6/1986 | St. John | 523/105 |
| 4,643,734 | 2/1987 | Lin | 623/16 |
| 4,677,191 | 6/1987 | Tanaka et al. | 528/361 |
| 4,683,288 | 7/1987 | Tanaka et al. | 528/361 |
| 4,719,246 | 1/1988 | Murdoch et al. | 521/134 |
| 4,727,163 | 2/1988 | Bellis | 549/274 |
| 4,728,721 | 3/1988 | Yamamoto et al. | 528/361 |
| 4,766,182 | 8/1988 | Murdoch et al. | 525/413 |
| 4,789,726 | 12/1988 | Hutchinson | 528/354 |
| 4,797,468 | 1/1989 | DeVries | 528/254 |
| 4,800,219 | 1/1989 | Murdoch et al. | 525/413 |
| 4,835,293 | 5/1989 | Bhatia | 549/274 |
| 4,902,515 | 2/1990 | Loomis et al. | 424/486 |
| 4,950,258 | 8/1990 | Kawai et al. | 604/281 |
| 4,960,866 | 10/1990 | Bendix et al. | 528/499 |
| 4,966,982 | 10/1990 | Ono et al. | 549/274 |
| 4,981,696 | 1/1991 | Loomis et al. | 424/486 |
| 4,983,745 | 1/1991 | Muller et al. | 549/274 |
| 4,990,222 | 2/1991 | Aigner et al. | 203/91 |
| 5,011,946 | 4/1991 | Hess et al. | 549/274 |
| 5,023,349 | 6/1991 | Bhatia | 549/274 |
| 5,023,350 | 6/1991 | Bhatia | 549/274 |
| 5,041,529 | 8/1991 | Shinoda et al. | 528/354 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,076,983 | 12/1991 | Loomis et al. | 264/101 |
| 5,097,005 | 3/1992 | Tietz | 528/272 |
| 5,108,399 | 4/1992 | Eitenmuller et al. | 606/77 |
| 5,132,397 | 7/1992 | DeGuia | 528/354 |
| 5,134,171 | 7/1992 | Hammel et al. | 521/98 |
| 5,136,017 | 8/1992 | Kharas et al. | 528/354 |
| 5,142,023 * | 8/1992 | Gruber et al. | 528/354 |
| 5,149,833 | 9/1992 | Hess et al. | 549/274 |
| 5,180,765 | 1/1993 | Sinclair | 524/306 |
| 5,229,528 | 7/1993 | Brake et al. | 549/274 |
| 5,236,560 | 8/1993 | Drysdale et al. | 203/99 |
| 5,264,614 | 11/1993 | Brake | 560/179 |
| 5,264,617 | 11/1993 | Brake | 560/179 |
| 5,264,626 | 11/1993 | Brake et al. | 562/589 |

FOREIGN PATENT DOCUMENTS

| | | |
|---|---|---|
| 267826 | 12/1913 | (DE) . |
| 1083275 | 12/1960 | (DE) . |
| 1543958 | 2/1970 | (DE) . |
| OS3632103 | 3/1988 | (DE) . |
| 01017591 | 2/1984 | (EP) . |
| 0299730 | 1/1989 | (EP) . |
| 0314245 | 5/1989 | (EP) . |
| 0052510 | 3/1992 | (EP) . |
| 0481732 | 4/1992 | (EP) . |
| 0507554 | 10/1992 | (EP) . |
| 0510998 | 10/1992 | (EP) . |
| 0515203 | 11/1992 | (EP) . |
| 1040168 | 8/1966 | (GB) . |
| 1108720 | 4/1968 | (GB) . |
| 1351409 | 5/1974 | (GB) . |
| 2145422 | 3/1985 | (GB) . |
| 4-283227 | 10/1992 | (JP) . |
| WO90/01521 | 2/1990 | (WO) . |
| WO91/02015 | 2/1991 | (WO) . |
| WO91/06601 | 5/1991 | (WO) . |
| WO92/00292 | 1/1992 | (WO) . |
| WO92/00974 | 1/1992 | (WO) . |
| WO92/04410 | 3/1992 | (WO) . |
| WO92/04412 | 3/1992 | (WO) . |
| WO92/04413 | 3/1992 | (WO) . |
| WO 92/05311 | 4/1992 | (WO) . |
| WO92/05167 | 4/1992 | (WO) . |
| WO92/05168 | 4/1992 | (WO) . |
| WO92/15340 | 9/1992 | (WO) . |
| WO91/17155 | 11/1992 | (WO) . |
| WO 93/02075 | 2/1993 | (WO) . |

OTHER PUBLICATIONS

Kulkarni et al. ("Biodegradable Poly(lactic acid) Polymers", May. 1971, *J. Biomed. Mater. Res.,* v. 5, pp. 169–181).

A. Schindler, R. Jeffcoat, G. Kimmel, C. Pitt, M. Wall, and R. Zweidinnger ("Biodegradable Polymers for Sustained Drug Delivery", Aug. 1977, *Contemporary Topics in Polymer Science,* v. 2, pp. 251–287).

I. Luderwald ("Thermal Degradation of Polyesters in the Mass Spectrometer", Dec. 1979, *Dev. Polymer Degradation,* v. 2, pp. 77–98).

M. Vert and F. Chabot, ("Stereoregular Bioresorbable Polyesters for Orthopaedic Surgery", Aug. 1991, *Makromol. Chem.,* Supp. 5, pp. 30–41).

M. Gupta and V. Deshmukh ("Thermal Oxidative Degradation of Poly–lactic Acid: Part I: Activation Energy of Thermal Degradation in Air", Apr. 1982, *Colloid & Polymer Science,* v. 260, pp. 308–311).

M. Gupta and V. Deshmukh ("Thermal Oxidative Degradation of Poly–lactic Acid; Part II: Molecular Weight and Electronic Spectra During Isothermal Heating", Mar. 1982, *Colloid & Polymer Science,* v. 260, pp. 514–517).

G. Van Hummel and S. Harkema ("Structure of 3,6–Dimethyl–1, 4–Dioxane–2,5–Dione [D–,D–{L–, L–}Lactide]", Jun. 1982, *Acta. Crystallogr.,* v. B38, pp. 1679–1681).

F. Chabot, M. Vert, S. Chapelle and P. Granger ("Configurational Structures of Lactic Acid Stereocopolymers as Determined by ⁻C($^1$H) N.M.R.", Jul. 1983, *Polymer,* v. 24, pp. 53–59).

F. Kohn, J. Van Don Berg, G. Van De Ridder and J. Feijen ("The Ring–Opening Polymerization of D,L–Lactide in the Melt Initiated with Tetraphenyltin", Sep. 1984, *Journal of Applied Polymer Science,* v. 29, pp. 4265–4277).

H. Kricheldorf and A. Serra ("Polylactones 6. Influence of Various Metal Salts on the Optical Purity of Poly(L–lactide)", Aug. 1985, *Polymer Bulletin,* v. 14, pp. 497–502).

A. Chawla and T. Chang ("In–Vivo Degradation of Poly (lactic acid) of Different Molecular Weights", Jan. 1985, *Biomat., Med. Dev., Art. Org.,* v. 13, pp. 153–162).

I. McNeill and H. Leiper ("Degradation Studies of Some Polyesters and Polycarbonates—1. Polylactide: General Features of the Degradation Under Programmed Heating Conditions", Jun. 1985, *Polymer Degradation and Stability,* v. 11, pp. 267–285).

I. McNeill and H. Leiper ("Degradation Studies of Some Polyesters and Polycarbonates—2. Polylactide: Degradation Under Isothermal Conditions, Thermal Degradation Mechanism and Photolysis of the Polymer", Aug. 1985, Polymer Degradation and Stability, v. 11, pp. 309–326).

Makino et al. ("Preparation and in Vitro Degradation Properties of Polylactide Microcapsules", Feb. 1985, *Chem. Pharm. Bull.*, v. 33, pp. 1195–1201).

D. Garozzo, M. Guiffrida and G. Montaudo ("Primary Thermal Decomposition Processes in Aliphatic Polyesters Investigated by Chemical Ionization Mass Spectrometry", Jun. 1986, *Macromolecules*, v. 19, pp. 1643–1649).

"Irganox® 1076 Antioxidant and Thermal Stabilizer", (published on an unknown date in 1986 by Ciba–Geigy Corporation, Three Skyline Drive, Hawthorne, NY 10532).

J. Leenslag and A. Pennings ("Synthesis of high–molecular–weight poly(L–lactide) initiated with tin 2–ethylhexanoate", Apr. 1987, *Makromol. Chem.*, v. 188, pp. 1809–1814).

Nakamura et al. ("Surgical Application of Biodegradable Films Prepared from Lactide–ε–Caprolactone Copolymers", Jun. 1987, *Bio. Materials and Clinical Applications*, v. 7, pp. 759–764).

H. Kricheldorf, M. Berl and N. Scharnagl ("Polymerization Mechanism of Metal Alkoxide Initiated Polymerizations of Lactide and Various Lactones", Jan. 1988, *Makromol.*, v. 21, pp. 286–293.

K. Jamshidi, S. Hyon and Y. Ikada ("Thermal Characterization of Polylactides", 2/1988, *Polymer*, v. 29, pp. 2229–2234).

M. Vert (Bioresorbable Polymers for Temporary Therapeutic Applications, 3/1989, *Die Angwandte Makromolekulare Chemie*, v. 166–167, pp. 155–168).

"Hydrolytic Stability/Corrosivity of Phosphite Costablizers", (Technical Bulletin 89–04, published on an unknown date in 1989, by Stars Laboratory, Additives Division, Ciba–Geigy Corporation, Ardsley, NY 10502).

"GE Specialty Chemicals Product Guide CA–4001E", (published on an unknown date in 1989, by General Electric Company, 5th and Avery Street, Parkersburg, WV 26102).

"Tinuvin® 123 Hindered Aminoether Light Stabilizer for Coatings", (published on an unknown date in 1989, by Ciba–Geigy Corporation, Three Skyline Drive, Hawthorne, NY 10532).

"Irganox® B–Blends Antioxidants and Process Stabilizers for Polymers", (published on an unknown date in Mar., 1990, by Ciba–Geigy Corporation, Three Skyline Drive, Hawthorne, NY 10532).

"Naugard® 445, Specialty Chemicals", (a product brochure published on or before May 1, 1990, by Uniroyal Chemical Company, Inc., Middlebury,CT 06749).

"Ethanox® 398 Antioxidant, The First Fluorophosphonite Antioxidant", (published on or before an unknown date in Oct., 1990, by Ethyl Corporation, 451 Florida Blvd., Baton Rouge, LA 70801).

"The Resomer® Resorbable Polyesters" (published on or before an unknown date in Feb., 1991 by Boehringer Ingelheim KG, D–6507 Ingelheim, W. Germany).

P. Klemchuk, ("Introduction to Polymer Degradation", lecture notes distributed at a seminer entitled: Principles of Polymer Degradation and Stabilization in Orlando, Florida, Oct. 28–30, 1991, sponsored by The Institute of Materials Science, State University of New York at New Paltz).

R. Thomas, ("Degradation and Stabilization of Engineering Polymers", lecture notes distributed at a seminar entitled: Principles of Polymer Degradation and Stabilization in Orlando, Florida, Oct. 28–30, 1991, sponsored by The Institute of Materials Science, State University of New York at New Paltz).

W. Enlow, ("Process Stabilization with Phosphite Antioxidants", lecture notes distributed at a seminar entitled: *Principles of Polymer Degradation and Stabilization* in Orlando, Florida, Oct. 28–30, 1991, sponsored by The Institute of Materials Science, State University of New York at New Paltz).

"Naugard® XL–1 Specialty Chemicals", (product brochure published on an unknown date in Feb., 1992, by Uniroyal Chemical Co., Inc., Middlebury, CT 06749).

Sir John Meurig Thomas, ("Solid Acid Catalysts", Apr. 1992, *Scientific American*, pp. 112–118).

"Argus Product Data, Argus® Dimyristyl Thiodipropionate", (published on or before an unknown date in Aug., 1992, by Argus Division, Witco Corporation, 633 Court Street, Brooklyn, NY 11231–2193).

"Argus Thiochemical Product Data, Argus® Thiodipropionate", (published on or before an unknown date in Aug., 1992, by Argus Division, Witco Corporation, 633 Court Street, Brooklyn, NY 11231–2193).

"Argus Product Data, Argus® Distearyl Thiodipropionate", (published on or before an unknown date in Aug., 1992, by Argus Division, Witco Corporation, 633 Court Street, Brooklyn, NY 11231–2193).

"Argus Product Data, Mark® 2140 Pentaerythrityl Octylthiopropionate", (published on or before an unknown date in Aug., 1992, by Argus Division, Witco Corporation, 633 Court Street, Brooklyn, NY 11231–2193).

"Argus Thiochemical Product Data, Argus® Dilauryl Thiodipropionate", (published on or before an unknown date in Aug., 1992, by Argus Division, Witco Corporation, 633 Court Street, Brooklyn, NY 11231–2193).

"Argus Product Data, Seenox® 412S Pentaerythritol Tetrakas (B–Laurylthiopropionate)", (published on or before an unknown date in Aug., 1992, by Argus Division, Witco Corporation, 633 Court Street, Brooklyn, NY 11231–2193).

"Irganox® 1010", (a product brochure published on or before an unknown date in Aug., 1992, by Ciba–Geigy Corporation, Three Skyline Drive, Hawthorne, NY 10532).

"Irganox® MD 1024, Metal Deactivator/Antioxidant", (published on an unknown date prior to Aug., 1992, by Ciba–Geigy Corporation, Three Skyline Drive, Hawthorne, NY 10532).

"Tinuvin® 622LD Low Dust, Hindered Amine Light Stabilizer for Polymers FDA–Cleared for Polyolefins", (published on an unknown date before Aug., 1992, by Ciba–Geigy Corporation, Three Skyline Drive, Hawthorne, NY 10532).

T. M. Jankanicz, "Polylactic Acid as a Biodegradable Carrier for Contraceptive Steroids", *Contraception*, vol. 8, No. 3, 227–234 (Jan. 1973).

A. D. Schwope et al., "Lactic/Glycolic Acid Polymers as Narcotic Antagonist Delivery Systems", *Life Sciences*, vol. 17, 1877–1886 (May 1975).

L. C. Anderson, "An Injectable Sustained Release Fertility Control Sy stem", *Contraception*, vol. 13, No. 3, 375–384 (Jun. 1976).

D. L. Wise et al., "Sustained Release of an Antimalarial Drug Using a Copolymer of Glycolic/Lactic Acid", *Life Sciences*, vol. 19, 867–874 (Aug. 1976).

R. A. Miller et al., "Degradation Rates of Resorbable Implants (Polylactates and Polyglycolates): Rate Modification with Changes in Pla/Pga Copolymer Rations", *J. Biomed. Mater. Res.*, vol. 11, 711–719 (Oct. 1977).

D. K. Gilding et al., Biodegradable Polymers for Use in Surgery—Polyglycolic/Polylactic Acid Homo and Copolymers: 1. *Polymer*, vol. 2, 1459–1464 (Dec. 1979).

D. K. Gilding, "Degradation of Polymers: Mechanisms and Implications for Biomedical Applications", *Biocompatibility of Clinical Implant Materials*, D. F. Williams, eds., vol. 1, 43–65 (Aug. 1981).

A. M. Reed and D. K. Gilding, "Biodegradable Polymers for Use in Surgery Polyglycolic/Polylactic Acid Homo and Copolymers: 2. In Vitro Degradation", *Polymer*, vol. 22, No. 4, 494–498 (Apr. 1981).

D. K. Gilding, "Biodegradable Polymers", *Biocompatibility of Clinical Implant Materials*, D. F. Williams, ed., vol. 2, 209–232 (Feb. 1981).

J. D. Strobel, "Biodegradable Polymers", paper presented at Medical Textiles and Biomedical Polymers and Materials Conference held at Clemson, S.C., U.S.A., Dec. 5–6, 1989, Stolle Research and Development Corp., PD 712–01, pp. 1–32 and Attachments A1–A21.

"Biocompatible Composite Would Be Completely Absorbed in the Body", *Advanced Materials*, vol. 12, No. 15, Aug. 1990, p. 6.

"Polylactides Exhibit Degradability", *Tappi Journal*, Sep. 1991, p. 42.

P.V. Bonsignore et al., Nov. 1992, "Poly(lactic acid) Degradable Plastics, Coatings and Binders", TAPPI Proceedings (Nonwovens Conference); pp. 129–140.

* cited by examiner

CONTINUOUS PROCESS FOR THE MANUFACTURE OF LACTIDE AND LACTIDE POLYMERS

This application is a continuation-in-part of U.S. application Ser. No. 07/935,059, which was filed on Aug. 24, 1992 and now U.S. Pat. No. 5,247,073. U.S. application Ser. No. 07/935,059 is a continuation-in-part of U.S. application Ser. No. 07/825,059, which was filed on Jan. 24, 1992 and issued on Aug. 25, 1992 as U.S. Pat. 5,142,023. Both U.S. application Ser. No. 07/935,059 and U.S. Pat. No. 5,142,023 are hereby incorporated by reference. Also hereby incorporated by reference is related U.S. application Ser. No. 07/935,566, which was filed on Aug. 7, 1992, allowed on May 18, 1993 and issued on Sep. 21, 1993 as U.S. Pat. No. 5,247,059.

BACKGROUND OF THE INVENTION

1. Field of the Invention

The present invention relates to processes for the continuous production of lactide and lactide polymers from crude lactic acid and esters of lactic acid in the field of biodegradable polymers.

2. Description of the Prior Art

The continued depletion of landfill space and the problems associated with incineration of waste have led to the need for development of truly biodegradable polymers to be utilized as substitutes for non-biodegradable or partially biodegradable, petrochemical-based polymers. The use of lactic acid and lactide to manufacture a biodegradable polymer is well known in the medical industry. As disclosed by Nieuwenhuis et al. (U.S. Pat. No. 5,053,485), such polymers have been used for making biodegradable sutures, clamps, bone plates and biologically active controlled release devices. It will be appreciated that processes developed for the manufacture of polymers to be utilized in the medical industry have incorporated techniques which respond to the need for high purity and biocompatibility in the final polymer product. Furthermore, the processes were designed to produce small volumes of high dollar-value products, with less emphasis on manufacturing cost and yield. It is believed that prior to Applicants' development, viable, cost-competitive processes for the continuous manufacture of purified lactide and lactide polymers from lactic acid having physical properties suitable for replacing present petrochemical-based polymers in packaging, paper coating and other non-medical industry applications were unknown.

It is known that lactic acid undergoes a condensation reaction to form polylactic acid when water is removed by evaporation or other means. The overall polymerization reaction is represented by:

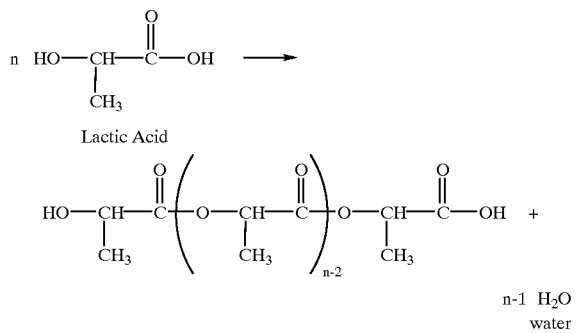

While step n of said polymerization reaction is represented by:

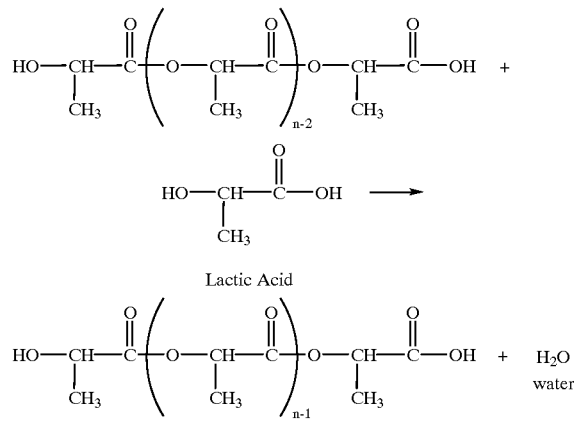

As Dorough (U.S. Pat. No. 1,995,970) recognized and disclosed, the resulting polylactic acid is limited to a low molecular weight polymer of limited value, based on physical properties, due to a competing depolymerization reaction in which the cyclic dimer of lactic acid, lactide, is generated. As the polylactic acid chain lengthens, the polymerization reaction rate decelerates until it reaches the rate of the depolymerization reaction, which effectively, limits the molecular weight of the resulting polymers. An example of this equilibrium reaction is represented below.

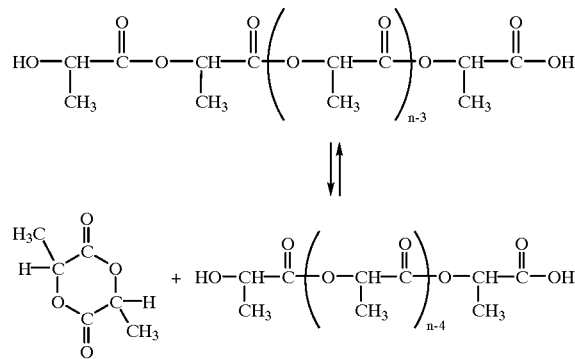

Given this understanding, Dorough was convinced that high molecular weight polymers could not be generated directly from lactic acid. He was, however, successful in generating high molecular weight polymers from lactide, through the lactic acid dimer generated from the low molecular weight polymers of lactic acid. Because these polymers are generated from lactide, they are known as polylactides.

It is well known that lactic acid exists in two forms which are optical enantiomers, designated as D-lactic acid and L-lactic acid. Either D-lactic acid, L-lactic acid or mixtures thereof may be polymerized to form an intermediate molecular weight polylactic acid which, upon further polymerization, generates lactide as earlier disclosed. The lactide, or the cyclic dimer of lactic acid, may have one of three types of optical activity depending on whether it consists of two L-lactic acid molecules, two D-lactic acid molecules or an L-lactic acid molecule and a D-lactic acid molecule combined to form the dimer. These three dimers are designated L-lactide, D-lactide and meso-lactide, respectively. In addition, a 50/50 mixture of L-lactide and D-lactide with a melting point of about 126° C. is often referred to in the literature as D,L-lactide.

DeVries (U.S. Pat. No. 4,797,468) recently disclosed a process for the manufacture of lactide polymers utilizing a solvent extraction process to purify lactide prior to polymerization. With DeVries' disclosure, the inventor recognized that existing literature recommends purification of lactide by several recrystallization steps. It is believed that processes prior to DeVries solvent extraction method, have generally utilized a recrystallization step to purify the crude lactide in order to obtain a source of lactide suitable for polymerization. However, processes utilizing such recrystallization steps are known to have relatively poor yields due to significant losses of lactide during the recrystallization steps. It is believed that producers of medical-related biodegradable products have not been concerned with such low yields because of the high margin generally expected for sales of such products and the lack of competitive alternatives. It will be appreciated, however, that in developing a process for the large-scale, commercial manufacture of biodegradable polymers, such as polylactides, for use in nonmedical-products-oriented applications where such polymers will necessarily compete with low-cost polymers made from petrochemicals, it will be important to maximize yield and minimize other overall cost factors to produce a biodegradable polymer which is cost-competitive.

The biodegradable polylactide polymers must also possess physical properties suitable for application in non-medical products presently utilizing petrochemical-based polymers such as packaging materials, paper coatings and any other disposable articles. Nieuwenhuis et al. disclose that lactide polymers derived from polymerization of mixtures of the three lactides result in polymers with a variety of useful physical properties, including improved biodegradability. However, no commercially viable process for the large-scale manufacture of such lactide polymers is believed to have been disclosed to date.

Lactic acid is commercially available and manufactured from several known processes. Representative examples of such processes are disclosed by Glassner et al. (European Pat. Application, EP 393818, Oct. 24, 1990), G. Machell, "Production and Applications of Lactic Acid", *Industrial Chemist and Chemical Manufacturer*, v. 35, pp. 283–90 (1959) and Kirk Othmer, *Encyclopedia of Chemical Technology*, "Lactic Acid", v. 12, pp. 177–78 (2nd ed. 1963).

The optical activity of either lactic acid or lactide is known to alter under certain conditions, with a tendency toward equilibrium at optical inactivity, where equal amounts of the D and L enantiomers are present. Relative concentrations of D and L in the starting materials, the presence of impurities or catalysts and time at varying temperatures and pressures are known to affect the rate of such racemization.

Muller (U.S. Pat. No. 5,053,522) discloses that the preparation of optically pure lactide from an optically pure lactic acid feed is possible when utilizing appropriate conditions and catalysts. However, it is believed that there are no teachings of processes that control the optical purity of the resulting lactide to desired degrees or minimizes overall costs and maximizes yield of the lactide product. Furthermore, it is believed that there are no disclosures, prior to work described in this and parent applications, of a commercially-viable lactide purification system, which allows production of polymer grade lactide, from crude lactic acid, which may subsequently be polymerized to produce a variety of non-medical-related polylactide polymers suitable for replacing existing petrochemical-based polymers.

Bellis (U.S. Pat. No. 4,727,163) discloses the use of an ester of an alpha-hydroxy acid on a thermally-stable polyether core to manufacture highly pure cyclic esters such as lactide. Bhatia (U.S. Pat. No. 4,835,293) discloses a process for preparing highly pure cyclic esters such as lactide by heating a polymer of the corresponding alpha-hydroxy acid or its ester or a copolymer of the alpha-hydroxy acid or its ester and a thermally-stable polyether core in the presence of an inert gas with the cyclic ester being carried from this reaction with the inert gas to a solvent system. Bellis et al. (PCT Application No. WO 92/00292, published Jan. 9, 1992) disclose a continuous catalyzed vapor phase process for the production of dimeric cyclic esters such as lactide by converting the corresponding alpha-hydroxy carboxylic acid or ester in the vapor phase over a solid catalyst such as silica alumina and preferably silica alumina having a high silica content, in the presence of a carrier gas. However, it is believed that none of these references disclose a commercially viable overall process for the large scale manufacture of polylactide polymers. Furthermore, there is no disclosure, prior to work described in this and parent applications, of a lactide generation system which allows production of a polymer grade lactide for use in non-medical-related polylactide polymers cost-effectively suitable for replacing existing petrochemical-based polymers.

SUMMARY OF THE INVENTION

The present invention provides a continuous process for the production of lactide polymers from a crude lactic acid feed source. The crude lactic acid feed may be any available combination of the optical enantiomers D-lactic acid and L-lactic acid in solution with a hydroxylic medium such as water or other solvent such as methanol, ethanol, propanol, butanol, isopropanol, isobutanol, or the like, or mixtures thereof. The crude lactic acid or source of lactic acid could also be an ester of lactic acid, such as methyl lactate, ethyl lactate, propyl lactate, butyl lactate, isopropyl lactate, isobutyl lactate or the like, or mixtures thereof. The crude lactic acid may also be a mixture of lactic acid and esters of lactic acid. An ester of lactic acid suitable for use in the present invention may generally be defined by the formula:

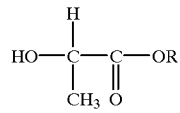

wherein R is a $C_1$–$C_8$ linear or branched alkyl.

When an ester of lactic acid is used as the source of a crude lactic acid for the process of the present invention, the polymerization reaction along with the depolymerization reaction and the equilibrium between the two compounds are altered. The ester group, or more particularly the linear or branched alkoxy group leaves during the polymerization reaction from one end of the lactate molecule while a hydrogen is cleaved from the hydroxy group on the opposite end of another lactate molecule. Thus, a condensation reaction by-product of the formula ROH is formed. The overall polymerization reaction is represented by:

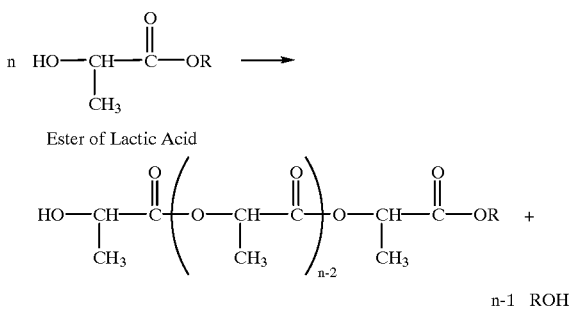

Ester of Lactic Acid

While step n of said polymerization reaction is represented by:

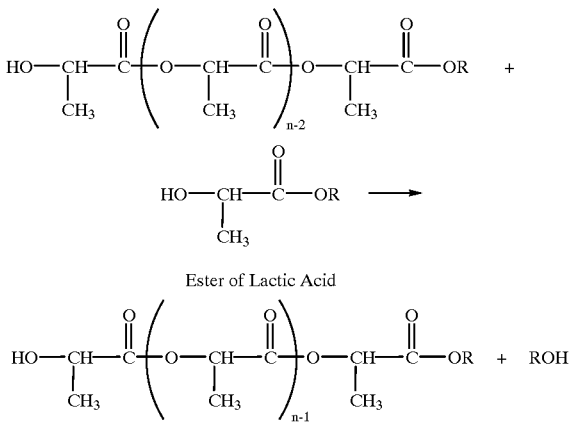

Ester of Lactic Acid

As the polylactic acid chain lengthens, the polymerization reaction rate decelerates and the depolymerization reaction to form lactide accelerates until equilibrium is reached. This equilibrium is represented by:

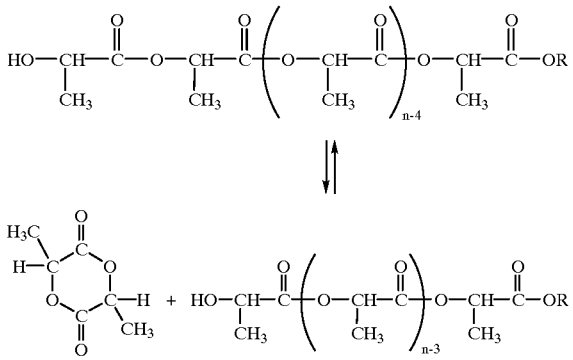

As indicated by the above reactions, polymer chains may contain an ester end group wherein said polymer would be defired as a polylactic ester polymer. For the sake of clarity, applicants herein define polylactic acid or polylactic acid molecules to include the polymer chains disclosed above with an ester end group or end cap as formed from the polymerization of an ester of lactic acid. Further, condensation reaction by-products include both water and chemical compounds of the general formula ROH wherein R is a $C_1$–$C_8$ linear or branched alkyl.

It is, however, recognized that the composition of the crude lactic acid feed source and the design and operating conditions of the process disclosed herein will affect the optical purity of the final polylactide polymer product. The process disclosed herein provides for the control of racemization to advantageously produce a polymer grade lactide of selected optical purity and composition.

Referring now briefly to FIG. 1, which provides a preferred flowchart of the overall process disclosed herein, the crude lactic acid is first fed to an evaporator, continuously. Within the evaporator a portion of the water or solvent or any condensation reaction by-product is removed from the crude lactic acid. The water or solvent or any condensation reaction by-product is removed as a vapor from the evaporator and discarded or recycled. The evaporator thus concentrates the lactic acid in the crude feed. It is believed there will be some condensation reaction occurring and the lactic acid may start to form oligomers and low molecular weight polymers during the evaporation step, producing a condensation reaction by-product. A small quantity of lactide may also form. This concentrated lactic acid is next fed to a prepolymer reactor, which in reality is a further evaporator.

It is well known in the art that as water or solvent are removed from a solution of lactic acid, the remaining lactic acid will begin to polymerize. In the prepolymer reactor, sufficient water or solvent and condensation byproducts such as water, ethanol, methanol, propanol, butanol, isopropanol, isobutanol and the like are removed to cause the lactic acid to polymerize to form lactic acid polymers having an average molecular weight of less than about 5000, preferably about 200 to about 3000, and more preferably about 400 to about 2500. The water or solvent removed is recycled or discarded. In preferred embodiments, the water or solvent is recycled back to the evaporation process, because it may be contaminated with lactic acid. In this preferred embodiment, loss of feed material is prevented and the overall yield is increased.

The prepolymer product from the prepolymer reactor, polylactic acid or PLA, is fed to a lactide reactor. The lactide reactor can be of any suitable type which is designed for heat sensitive materials. A reactor that can maintain a uniform film thickness, such as a falling film or agitated thin-film evaporator is most preferred, because film formation increases the rate of mass transfer. When the rate of mass transfer is increased, lactide can quickly form and vaporize, and as lactide vaporizes, more lactide is produced as dictated by the polylactic acid/lactide equilibrium reaction.

Preferably, an evaporator is used that can maintain a film thickness in the reaction or mass transfer zone of at least about 0.5 mm and not greater than about 15 mm. An evaporator than can maintain a film thickness in the reactor's mass transfer zone of at least about 0.5 mm and no greater than about 8 mm is most preferred. In a preferred embodiment, the lactide reactor operates at a reduced pressure. Preferably, the pressure of the environment within the reactor is at least about 1 mm Hg and not greater than about 100 mm Hg, and most preferably at least about 2 mm Hg and not greater than about 60 mm Hg.

In accordance with the present invention, the residence time of the polylactic acid in the lactide reactor is as low as reasonably possible. Preferably, the reactor mean residence time is at least about 1 minute and not greater than about 45 minutes, and more preferably at least about 2 minutes and not greater than about 20 minutes. Most preferably, the lactide reactor mean residence time is at least about 2.5 minutes and not greater than about 10 minutes. A process in accord with the present invention, can accommodate a wide variety of mass flow rates through the reactor. Typically, reactor feed flow rates from 1 lb/hr to 30,000 lb/hr can be maintained.

A catalyst is simultaneously and continuously fed to the lactide reactor. Many suitable catalysts are known, such as metal oxides, metal halides, metal dusts and organic metal compounds derived from carboxylic acids or the like. It is believed, any such catalyst may be utilized in the process disclosed herein. Polymer properties will, however, vary. In a preferred embodiment, the prepolymer and catalyst are mixed together in a static mixer to facilitate an even distribution of catalyst within the prepolymer, and the catalyst would comprise at least about 0.05% and not more than about 10% by weight of the catalyzed polylactic acid solution. The solution within the lactide reactor would quickly come to an equilibrium distribution of lactide and polylactic acid with the temperature and catalyst employed. In a preferred embodiment, process stabilizers can also be added to the catalyzed polylactic acid prior to the feed entering the lactide reactor. A variety of process stabilizers can be used. Preferably, phosphite-containing compounds, hindered phenolic compounds, or other phenolic compounds are used as process stabilizing antioxidants. Most preferably, phosphite-containing compounds are used. The amount of process stabilizer used can vary. Preferably, at least about 0.01 wt % and no greater than -about 1 wt % is used. Most preferably at least about 0.025 wt % and no greater than about 0.3 wt % is used.

Heat is added to vaporize the crude lactide which is continuously removed from the lactide reactor, thus driving the depolymerization reaction, resulting in the net production of lactide as the contents of the lactide reactor seek equilibrium. It is believed that concentrations of unreactive high-boiling polylactic acid and other non-volatile impurities, catalyst residues, antioxidant residues (if process stabilizers, such as antioxidants are used), metals accumulated from the lactic acid feed and reactor leaching, color bodies, and lactic acid degradation products will concentrate in the solution within the lactide reactor. It is believed this will require a purge stream to remove such impurities.

In a preferred embodiment of the present invention, a portion of the purge stream of unreactive high-boiling polylactic acid or other non-volatile impurities in the solution within the lactide reactor may be recycled to a point prior to the lactide reactor system or fed to polymerization. Based on experimental data which will follow hereinbelow, it is believed that any long chain lactic acid polymers will undergo transesterification to form lower molecular weight polylactic acids which may be utilized as a feed source to the lactide reactor. Treatment of the purge stream can be used to remove many of the impurities such as catalyst residues, antioxidant residues, color bodies, metals, and degradation products. This allows further maximization of yield due to reduced loss of valuable feed material.

The crude lactide vapor is composed of a mixture of all three possible lactides: L-lactide, D-lactide, and meso-lactide, in various combinations. Along with the lactide, there is residual water, lactic acid and condensation reaction byproducts. In a preferred embodiment, this crude lactide is fed directly to a distillation system as a vapor for purification. Alternatively, this stream may be fed to a partial condenser in which the lactide condenses and the majority of the water and other impurities remain as vapors and are recycled back to the lactide reactor or other upstream process equipment such as the evaporator or prepolymer reactor. Preferably, the crude lactide is fed directly to a distillation system for purification. Within this distillation system residual water and lactic acid are preferably removed as a distillate product and recycled back to the lactide reactor or other upstream process equipment such as the evaporator or prepolymer reactor. In addition, provision may be made to remove low molecular weight oligomers which may be present in the crude lactide or formed during distillation. The purified lactide is preferably fed to a polymerization reactor of conventional design.

The preferred overall process disclosed herein allows for the continuous manufacture of lactide polymers from a crude lactic acid with little or no waste of raw material lactic acid feed or ester of lactic acid feed. This is accomplished by maintaining the crude lactide which was generated in the lactide reactor as a liquid or vapor and avoiding the yield loss associated with the recrystallization step traditionally used to purify the lactide. The purified lactide leaving the distillation system is further maintained as a liquid and fed into a polymerization process.

In particular, this system allows recovery of any meso-lactide which may be present or formed within the disclosed process and which is normally lost in a recrystallization process. Further, the problems associated with handling solid materials are eliminated. These problems are well-documented by D. D. Deane and E. G. Hammond in "Coagulation of Milk for Cheese-Making by Ester Hydrolysis", *J. Dairy Science*, v. 43, pp. 1421–1429 (1960) and Nieuwenhuis et al. (U.S. Pat. 5,053,485) which are incorporated herein by reference. The problems of storing such solids for any time period are also disclosed by Deprospero et al. (U.S. Pat. 3,597,449) and F. E. Kohn et al. in *J. of Applied Polymer Science*, Vol. 29, 4265–4277 (1984) which are incorporated herein by reference. These problems include contamination by water vapor which would lead to ring-opening side reactions causing the lactide to convert to lactic acid. The presence of lactic acid in the feed to the final polymerization step will result in polymers of limited molecular weight.

Applicants believe that one would not turn to utilization of distillation due to the narrow differences between melting point and boiling point of lactide streams, which potentially could cause solid plugging problems within a distillation system. Furthermore, side reactions in which the lactide ring is opened and polymers of lactic acid are formed may occur during distillation. It is believed, the presence of such side reaction products would lead to undesirable molecular weight limitations in the final polymer product. Applicants have discovered that proper design and control of a distillation system coupled with direct feed of a crude lactide vapor stream or a liquid crude lactide stream after partial condensation to remove water and lactic acid vapor allows purification of crude lactide in a conventional distillation system. Previous to this disclosure, applicants believe, any polymer made from non-optically pure lactide relied on blending the various lactide components, each of which had been purified separately using recrystallization of a crude lactide produced by other techniques.

These and various other advantages and features of novelty which characterize the present invention are pointed out with particularity in the claims annexed hereto and forming a part hereof. However, for a better understanding of the invention, its advantages, and the objects attained by its use, reference should be made to the drawings which form a further part hereof, and to the accompanying descriptive matter, in which there are illustrated and described preferred embodiments of the present invention.

BRIEF DESCRIPTION OF THE DRAWINGS

In the drawings, in which like referenced numerals indicate corresponding parts or elements of preferred embodiments of the present invention throughout the several views.

DETAILED DESCRIPTION OF THE PREFERRED EMBODIMENTS

As required, detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one skilled in the art to variously practice the present invention.

Figure 1:
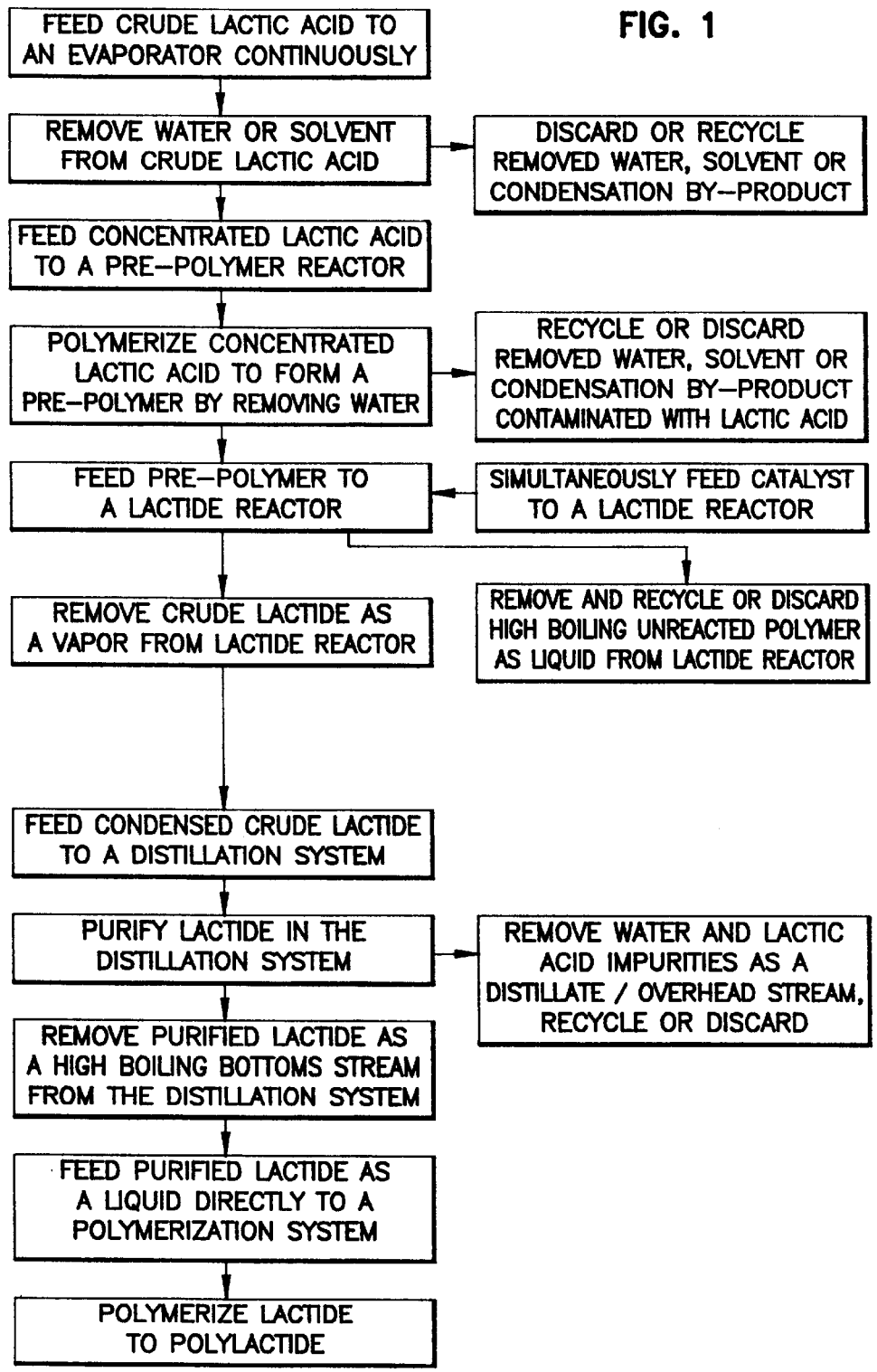
FIG. 1 is a flow diagram of the preferred overall process steps of the present invention.
Figure 2:
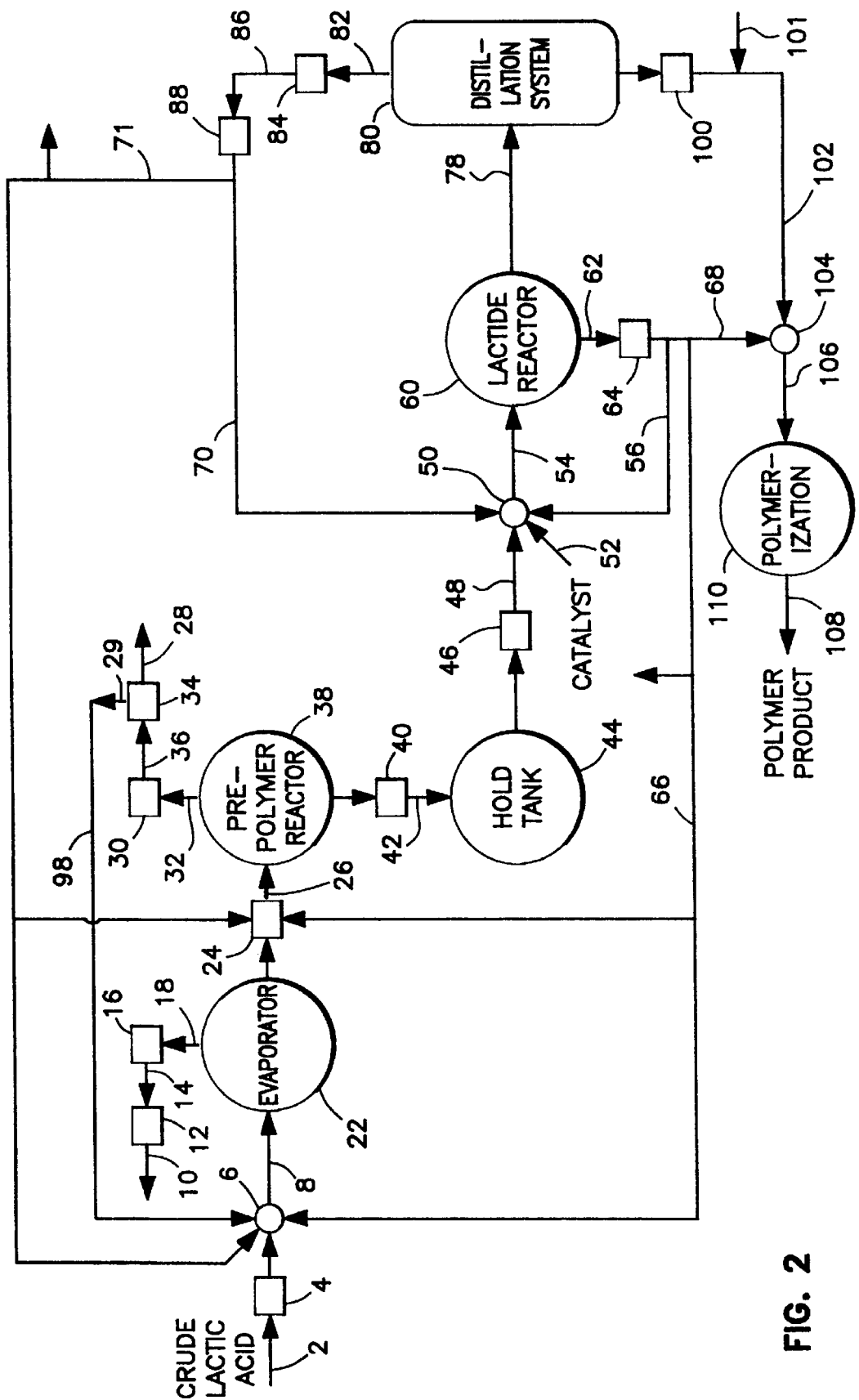
FIG. 2 is a detailed schematic representation of a preferred polylactide polymer production system in accordance with the present invention.

Referring now to the figures, FIG. 2 represents an overall schematic flowchart encompassing the preferred process disclosed herein. A crude lactic acid feed (2) is provided. The crude lactic acid feed may be of various grades. This could include USP, food grade, or any other solution in a hydroxylic medium. A hydroxylic medium is a medium which contains molecules having a hydroxyl group, mediums such as water, methanol, ethanol, propanol, butanol, isopropanol, isobutanol and the like, preferably having a number of carbon atoms in a range from 0–4, more preferably in a range from 0–2. The crude lactic acid can include from about 1% to about 99% by weight lactic acid, preferably, from about 1% to about 85%, more preferably from about 5% to about 50%. In a preferred embodiment, the crude lactic acid feed is a solution of about 15% lactic acid and about 85% water which is commercially produced. Many manufacturing processes for producing crude lactic acid are known in the art, such as Glassner et al., (European Pat. Application, EP 393818, Oct. 24, 1990); G. Machell, "Production and Applications of Lactic Acid", *Industrial Chemist and Chemical Manufacturer*, v. 35, pp. 283–90 (1959) and Kirk Othmer, *Encyclopedia of Chemical Technology*, "Lactic Acid", v. 12, pp. 177–78 (2nd ed. 1963), which are incorporated herein by reference. In an alternative embodiment, the source of crude lactic acid (2) could be in the form of the ester of lactic acid of the general formula:

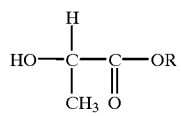

wherein R is a $C_1$–$C_8$ linear or branched alkyl. Preferred esters are methyl lactate, ethyl lactate, propyl lactate, butyl lactate, isopropyl lactate or isobutyl lactate or mixtures thereof. These esters are known intermediate products of the lactic acid process disclosed above and incorporated herein by reference. The crude lactic acid may be a mixture of these esters of lactic acid or a mixture of these esters of lactic acid or a mixture of one or more esters of lactic acid with lactic acid.

A fluid transfer mechanism (4) in FIG. 2 is provided to transport the crude lactic acid feed (2) through an optional in-line mixer (6) in a pipeline (8) to an evaporator system (22). The evaporator system (22) is utilized to concentrate the crude lactic acid feed (2) by removing water or any other solvent or hydroxylic medium which is used as a carrier for the lactic acid, such as methanol, ethanol or the like and any condensation reaction by-products. The evaporator system (22) may be of any conventional type known in the art, such as a multiple effect evaporator, an agitated thin-film evaporator, a falling film evaporator, or any other conventional system. It is appreciated that such systems may be operated at pressures below atmospheric pressure, at atmospheric pressure or above atmospheric pressure with commensurate changes in heat load and operating temperatures. In a preferred embodiment, vacuum evaporation is utilized to reduce racemization. Water vapor or solvent vapor, in reference to the hydroxylic medium or condensation reaction by-product, is removed from the evaporator via a transfer line (18), and condensed in a condenser (16). The condensed liquid is transferred in a pipeline (14) to a fluid transfer mechanism (12), such as a pump or the like. The fluid transfer mechanism (12) transports the condensed water or solvent via pipeline (10) as a waste stream and is discarded.

The lactic acid may be concentrated to a weight percent lactic acid of about 50% to about 99%, preferably from about 75% to about 99% and more preferably from about 85% to about 99%. In a preferred embodiment, the evaporator system (22) is utilized to concentrate the crude lactic acid feed from about 15% lactic acid up to about 85% lactic acid.

The concentrated lactic acid is transferred via a fluid transfer mechanism (24) through a pipeline (26) to a prepolymer reactor (38). The prepolymer reactor (38) is essentially a second evaporator system of any conventional type which is utilized to further remove water or solvent from the crude lactic acid feed. A portion of the water or solvent vapor now also includes such water or solvent produced from the lactic acid polymerization reaction previously disclosed, the condensation reaction by-product. The water or solvent vapor leaves the prepolymer reactor (38) via line (32) and is condensed in a condenser (30). The condensed liquid is transferred via pipeline (36) to a transfer mechanism (34), with the transferred liquid comprising water or solvent with small amounts of lactic acid and other impurities present. This liquid may be discarded through line (28) or may be recycled through line (29) back to a static mixer or other mixing mechanism and fed once again through line (8) to the evaporator (22). The remaining liquid in the prepolymer reactor is continuously transferred via transfer mechanism (40) through line (42) to a hold tank (44).

As previously disclosed, it is well recognized in the art that lactic acid undergoes a condensation reaction to form polylactic acid, the polymer of lactic acid, as water is removed. In a preferred embodiment of the present system, the prepolymer reactor (38) is utilized to remove adequate water or solvent and condensation reaction by-product from the lactic acid to cause polymerization up to a molecular weight of less than about 5000, preferably about 200 to about 3000, and more preferably about 400 to about 2500. As will be detailed in Example 2, which follows, in preferred embodiments the molecular weight of the polylactic acid leaving the prepolymer reactor impacts the chemical purity as well as the optical purity of the crude lactide. This in turn will affect the distillation and the properties of the final polymer product Applicants recognize that the evaporator system (22) and the prepolymer reactor (38) could be combined into a single system which provided removal of water or solvent sufficient to concentrate the lactic acid feed and also to polymerize such lactic acid. In the preferred embodiment, as discussed above, the systems are separate to take advantage of recognized differences in the composition of the vapor leaving the evaporator (22) at line (18) and the vapor leaving the prepolymer reactor (38) in line (32). The first step of concentrating the crude lactic acid in the evaporator (22) from 15% lactic acid to 85% lactic acid results in substantially pure water or solvent leaving the evaporator in line (18), which may be readily discarded without treatment. The vapor in line (32) leaving the prepolymer reactor (38) will necessarily contain lactic acid and other impurities which are carried over in the evaporation process. These impurities will preferably need to be recycled or treated before discarded. Thus, in the preferred embodiment, Applicants take advantage of the economic benefits of removing nearly pure water (or solvent) in the evaporator (22) and reduced recycle or waste treatment of the vapor leaving the prepolymer reactor (38).

Applicants also recognize that the evaporator system (22) and pre-polymer reactor (38) may be replaced by a series of batch evaporators that concentrate the lactic acid and produce pre-polymer. The series of batch systems may be operated to provide a net continuous supply of pre-polymer.

The hold tank (44) is maintained at a temperature sufficient to keep the polylactic acid in a flowable liquid state. The hold tank (44) is, however, only a feature of the preferred embodiment, recognizing the control problems which may result from direct feed to the lactide reactor (60). This liquid is transferred via transfer mechanism (46) through a pipeline (48) to a static in-line mixer or other mixing mechanism (50). Within the mixing mechanism (50) a catalyst is added to the polylactic acid. Applicants recognize that any means of adding the catalyst to the polylactic acid would be appropriate; however, the static mixer (50) utilized in the preferred embodiment allows more even distribution of the catalyst within the liquid. The catalyzed polylactic acid is transferred via transfer line (54) to the lactide reactor (60). It is well recognized in the art that polylactic acid maintains a dynamic equilibrium with its depolymerization product, lactide, as represented by the reaction below:

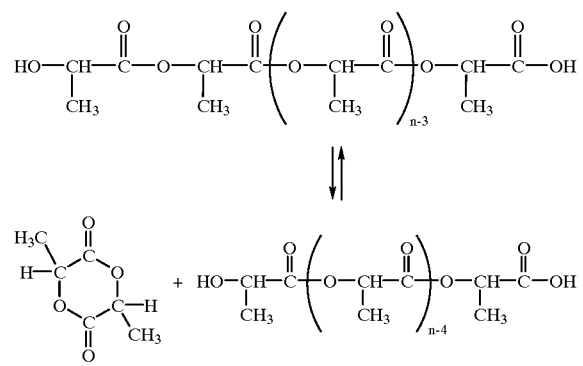

It is further recognized that this reaction is catalyzed by such compounds as tin dust, tin halide, tin oxide, and organic tin compounds derived from $C_1$–$C_{20}$ carboxylic acids, as disclosed by Muller in U.S. Pat. No. 5,053,522, which is incorporated herein by reference. Other metals, such as zinc, and their halides, oxides and organic compounds thereof, have been recognized by the art as possible catalysts for the lactide reaction. It is believed any metals of Groups IV, V or VIII of the Periodic Table and compounds thereof, are possible catalysts for generating lactide. In a preferred embodiment a tin-containing catalyst, such as tin(IV) butyltin tris(2-ethylhexanoate) (available as FASCAT® 9102 from Atochem North America Inc, Philadelphia, Pa.) is used. The amount of catalyst required to facilitate lactide formation can vary with the composition and molecular weight of the polylactic acid feed transferred through pipeline (48). However, it is believed that the catalyzed polylactic acid stream transferred through pipeline (54) should comprise at least about 0.05% and no more than about 10%, by weight, catalyst, and preferably at least about 0.1% and no more than about 5% by weight.

Process stabilizers may also be added to the static mixer (50) in order to facilitate lactide formation and discourage degenerative lactic acid and lactide reactions. Process stabilizers, such as antioxidants, can be used to reduce the number of degradation reactions that occur during the process of polylactic acid and lactide production. Process stabilizers may also, unfortunately, reduce the rate of lactide formation during this process. Therefore, efficient production of lactide requires proper reactor design for minimal thermal severity and a proper balance between the catalyst and any use of process stabilizers. A variety of process stabilizers may be used. The stabilizing agent may include primary antioxidants and/or secondary antioxidants. Primary antioxidants are those which inhibit free radical propagation reactions, such as alkylidene bisphenols, alkyl phenols, aromatic amines, aromatic nitro and nitroso compounds, and quinones. Secondary (or preventive) antioxidants breakdown hydroperoxides to prevent formation of free radicals. Some examples of secondary antioxidants include: phosphates, organic sulfides, thioethers, dithiocarbamates, and dithiophosphates. Antioxidants, when added to the lactic acid in static mixer (50) can reduce the extent of racemization during lactide production. This reduction indicates that the addition of antioxidants are an additional means to control optical purity. Antioxidants include such compounds as trialkyl phosphites, mixed alkyl/aryl phosphites, alkylated aryl phosphites, sterically hindered aryl phosphites, aliphatic spirocyclic phosphates, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones and mixtures thereof. Preferably, phosphite-containing compounds, hindered phenolic compounds, or other phenolic compounds are used as process stabilizing antioxidants. Most preferably, phosphite-containing compounds are used. The amount of process stabilizer used can vary depending upon the optical purity desired of the resulting lactide, the amount and type of catalyst used, and the conditions inside of the lactide reactor (60). Preferably, the feed to the lactide reactor (60) comprises at least about 0.01 wt % process stabilizers and not greater than about 1 wt %, and most preferably at least about 0.025 wt % and not greater than about 0.3 wt %.

The lactide reactor (60) can be any type of reactor that is suitable for producing lactide. An evaporator is preferred, because once the lactide is formed in the reactor, it can be vaporized, and transferred to the distillation system (80) for purification. Some examples of well-known evaporators, some of which are disclosed in FIG. 11–21 of *Perry's Chemical Engineer's Handbook,* 6th ed. (1984) which is incorporated herein by reference, that are useable in the present invention include: forced circulation, short path or short tube, long-tube vertical, long-tube horizontal, falling film, agitated thin-film, and disk evaporators.

Figure 6:
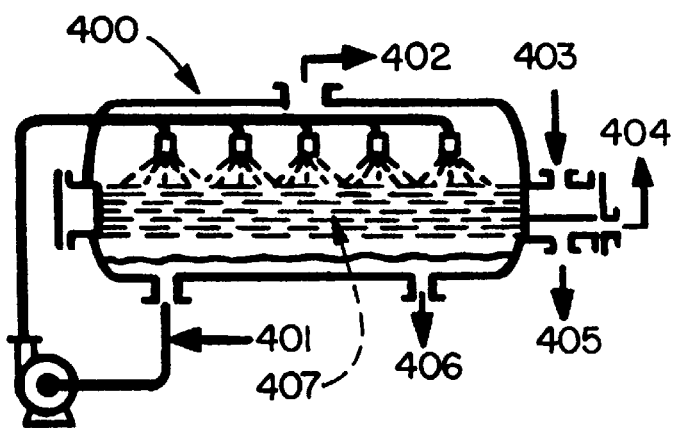
FIG. 6 is a schematic representation of a horizontal tube reactor system.

For example, FIG. 6 provides a schematic representation of a horizontal-tube evaporator (400). In this configuration, the catalyzed polylactic acid feed transferred through pipeline (54) comprises the liquid (401) that is fed into the system. This catalyzed polylactic acid feed (401) is sprayed onto the horizontal tubes (407), while a heat transfer fluid, such as steam (403) is fed into the horizontal tubes (407), condenses and exits as condensate (405). A vent (404) is provided for the system. As the polylactic acid feed (401) is sprayed onto the heated horizontal tubes (407), heat is transferred to the liquid, and the lactide that is formed vaporizes and exits the reactor system as vapor (402) with any other relatively volatile materials, such as water or solvent. The portion of the catalyzed polylactic acid feed (401) that does not vaporize and exit the system as vapor (402), flows down the horizontal tubes (407) and exits the system as liquid (406). This liquid (406) may be recycled back into the reactor system or discarded.

In order to facilitate the transfer of lactide vapor out of the lactide reactor (60), the reactor (60), in a preferred embodiment, is operated at a partial vacuum at a pressure of at least about 1 mm Hg and not greater than about 100 mm Hg. Most preferably, the reactor system is operated at a pressure that is at least about 2 mm Hg and not greater than 60 mm Hg. Therefore, the lactide vapor can promptly exit the system through pipeline (78). Once inside of the reactor (60), the temperature of the catalyzed polylactic acid feed that is transferred through pipeline (54) into the reactor should be such that lactide can be readily formed. Preferably, once inside of the reactor, the feed should be at least about 180° C. and not greater than about 300° C. Most preferably, the feed is at least about 180° C. and not greater than 250° C. during steady state operation.

It is an object of the present invention to keep lactide reactor (60) mean residence time as low as reasonably possible. Therefore, evaporators that can decrease mean reactor residence time as much as possible are preferred. Preferably, at steady state operation, the lactide reactor (60) mean residence time is at least about 1 minute and not greater than about 45 minutes, and more preferably at least about 2 minutes and not greater than about 20 minutes. Most preferably the lactide reactor mean residence time is at least about 2.0 minutes and not greater than about 10 minutes. In the present application, lactide reactor (60) mean residence time is taken to be the ratio of the liquid hold-up in the reactor to the rate of crude lactide produced. The lactide reactor (60) mean residence time can be measured or calculated by methods well known in the art. A process in accord with the present invention can accommodate a wide variety of flow rates through the lactide reactor (60). Typically, flow rates from about 1 lb/hr to about 30,000 lb/hr can be accommodated in various size lactide reactors.

Film generating evaporators are preferred because polylactic acid and lactide are heat sensitive materials. As the amount of heat to which these materials are exposed increases, the number of degenerative polylactic acid and lactide reactions is likely to increase, and the lactide yield will more than likely decrease. In general, film generating evaporators have relatively low hold-up times and high heat transfer coefficients, both of which decrease the number of degenerative side reactions that occur during lactide production.

Falling film and agitated thin-film evaporators are most preferred. Falling film or agitated thin-film evaporators in which a film of less than about 15 mm forms in the reaction or heat transfer zone are preferred. Most preferred are falling film evaporators or agitated thin-film evaporators in which a film of less than about 8 mm forms in the reaction or heat transfer zone. Agitated thin-film evaporators include all mechanically agitated film evaporators, including those that use rollers, wipers, or rotors with no wall contact.

Figure 7:
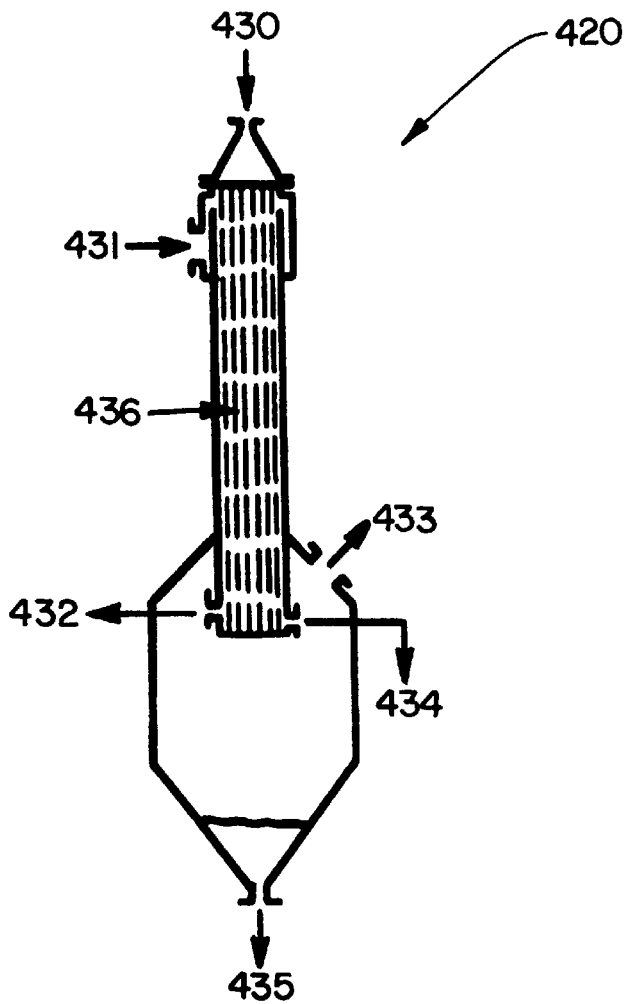
FIG. 7 is a schematic representation of a preferred falling film reactor system.

FIG. 7 provides a schematic representation of a preferred configuration of a falling film evaporator (420). In FIG. 7, the polylactic acid feed (430) enters at the top of the evaporator, flows down the long vertical tubes (436) which comprise the heat transfer or reaction zone, and exits at the bottom of the tubes where the vapor containing lactide (433) exits the system. Steam (or other heat transfer fluid) (431) enters the system, condenses, and exits as liquid (434). Steam (or other heat transfer fluid) that does not condense during heat transfer can exit as vapor (432).

The less volatile and unconverted portions of the polylactic acid feed fall from the bottom of the tubes into the liquid tank and exit the system as liquid (435). In general, the film thickness in a falling film evaporator is determined by the rate at which the liquid flows down the tubes. If the liquid is relatively viscous, then the film will be thicker because the liquid will flow slower. If the liquid is not relatively viscous, then the film will be thinner because the liquid will flow faster. A thinner film thickness is preferred because, in general, heat moves more quickly across a thinner film (e.g. 0.5 mm to 15 mm), and more lactide molecules can vaporize in a shorter period of time. When heat moves more quickly across the film, vaporizing more lactide molecules, reactor residence time can be minimized. A thinner film is also preferred because it will have a smaller temperature gradient across it, meaning that there will be less likelihood of charring or fouling at the heat transfer surface for a given mean temperature.

Optionally, a film reactor, may be oriented horizontally and/or contain an agitation system that uniformly distributes the liquid within the heat transfer and reaction zone. Moreover, the agitation system may continuously refresh the liquid film on the heat transfer surface in order to maximize mass transfer and to minimize holdup and reactor residence times. A horizontally or vertically oriented agitated thin-film reactor is most preferred in order to maximize lactide production and minimize lactide reactor residence time.

In addition, to an agitation system, a film reactor system, in accordance with the present invention, may also contain an internal condenser, which would condense the lactide-containing vapor prior to its exit from the reactor system. Thus, the stream exiting the lactide reactor system (60) via line (78) would be a liquid instead of a vapor. Applicants also recognize that more than one reactor can be utilized in the reactor system in accord with the present invention.

As lactide is generated within the lactide reactor (60), it is removed as a vapor continuously through line (58). The removal of lactide further drives the depolymerization reaction. It is believed that some high-boiling or non-volatile contaminants present in the feed to the entire system will concentrate in the lactide reactor and necessitate inclusion of a purge stream (62). The purge stream flowing from the lactide reactor (60) through pipeline (62) would contain polymerized lactic acid, catalyst residues, antioxidant residues (if process stabilizers such as antioxidants are used), and metals accumulated from the lactic acid feed and reactor leaching. Treatment of the purge stream can be used to remove many of the impurities such as catalyst residues, antioxidant residues, color bodies, metals, and degredation products. The purge stream is hydrolyzed in any suitable reactor at a temperature from about 100° C. to about 200° C. with a mean residence time of about 0.5 to about 4 hours. Preferably, one or more backmixed reactors are used. The hydrolyzed purge stream is then either decanted, filtered, centrifuged, or separated by any other means well-known in the art into a clear supernatant and a solid precipitate. The solid precipitate, which contains the bulk of the metals present in the purge stream, can be treated to recover the metals by any well-known means. The supernatant is treated, for example, with carbon and/or with an ion exchange resin, to remove residual impurities such as color bodies, lactic acid degradation products, and residual metals. The purified lactic acid can then be recycled to an upstream portion of the process, such as the prepolymer reactor (38), optional mixer (24) or the lactic acid evaporator (22), if additional treatment is required.

Example 7 below details the detrimental effects of concentrating metal ions in the lactide reactor (60). It is believed other impurities would have a similar effect and necessitate the purge stream (62). A portion of this purge stream (56) may be recycled back to the static mixer (50) and recatalyzed and fed to the lactide reactor (60). Alternatively, the purge stream may be fed to the polymerization reactor (110) via line (68), if such polymer is desired. A transfer mechanism (64) is provided to transport the purge stream optionally to a point prior to the evaporator (22) such as the static mixer (6) or to the feed line (26) to the prepolymer reactor (38) or to waste through line (66) or to a static mixer (104) for polymerization in a polymerization reactor (110).

The lactide vapor leaving the lactide reactor (60) in line (78) consists of residual lactic acid and water or solvent, along with some lactide. This vapor stream leaves the system through line (78) and directly enters the distillation system. In another embodiment, the lactide vapor could be partially condensed in a condenser, from which the liquid lactide could be fed to the distillation system, and the resulting vapors could be discarded or recycled back to the crude lactic acid static mixer (6). Preferably, this stream would be recycled in order to recover and utilize any lactic acid or lactide that had not been condensed.

The crude lactide vapor leaving lactide reactor (60) via line (78) is transferred to a distillation system (80) for purification of the lactide. The distillate leaving the distillation system (80) in line (82) is composed of water or solvent, some residual lactic acid, and some lactide carryover. This stream is condensed in condenser (84) and transferred via fluid transfer mechanism (88), in line (86), and may be discarded or recycled back to a point prior to the evaporator (22), such as the static mixer (6) or the feed line (26) to the prepolymer reactor (38) through line (71), or more preferably recycled in line (70) back to the static mixer (50) to be recatalyzed and re-fed to the lactide reactor (60). This preferred embodiment allows minimization of waste by preventing loss of lactic acid or converted lactic acid to lactide from the feedstock.

The refined lactide is removed from the distillation system (80) via transfer mechanism (100) in line (102) and fed to a polymerization reactor (110). Applicants recognize that the distillation system (80) may include more than one distillation column or a flash drum.

As previously disclosed, it may be necessary to subject the substantially purified lactide to further purification in a second distillation system prior to polymerization. One of skill in the art would make this decision based on design and operation of the first distillation system in light of desired final polymer properties. For example, in order to obtain the desired final polymer properties, it may be necessary for meso-lactide to be separated from L and D lactide. Therefore, the substantially purified lactide would be further distilled to form at least two purified lactide streams, one meso-lactide enriched and one meso-lactide depleted. This further distillation could be used to produce polymers of different compositions.

The polymerization process may be of any conventional design known to the art, such as that disclosed by J. Leenslag and A. Pennings, "Synthesis of High Molecular Weight Poly (L-lactide) Initiated with Tin 2-Ethylhexanoate", *Makromol. Chem.*, v. 188, pp. 1809–14 (1987) and F. Kohn et al., "The Ring-Opening Polymerization of D,L-Lactide in the Melt Initiated with Tetraphenyltin, J. Applied Polymer Science, v. 29, pp. 4265–77 (1984), which are incorporated herein by reference.

Applicants recognize that in a preferred embodiment one may choose to add a non-lactide monomer to the purified lactide leaving the distillation system (80). This co-monomer may be added via line (101). The co-monomers are fed to the polymerization reactor (110) and polymerized to form a co-polymer. Many co-polymers of polylactide are known to the art. These include P. Dave, N. Ashar, R. Gross, S. McCarthy, "Survey of Polymer Blends Containing Poly (3-hydroxybutyrate-co-16% hydroxyvalerate), *Polymer Preparation, American Chemical Society*, v. 31 (1), pp. 442–3 (1990); B. Riedl and R. Prud'homme, "Thermodynamic Study of Poly(vinyl chloride)-Polyester Blends by Inverse Gas Phase Chromatography", *J. Polymer Science*, Part B, vol. 24(11), pp. 2565–82 (1986); H. Younes and D. Cohn, "Phase Separation in Poly(ethylene glycol)/Poly (lactic acid) Blends, European Polymer J., v. 24(8), pp. 765–73 (1988); Smith et al. (European Pat. Application, EP 209371, Jan. 21, 1987); Pines et al. (European Patent Application EP 109197, May 23, 1984); J. Zhu, Y. Shao, W. Sui, S. Zhang, H. Xiao and X. Tao, "Homopolymers and Copolymers of Glycolide and Lactide", C-MRS Int. Symp. Proc. Meeting Date 1990, v. 3, pp. 387–90 (1990); Jarrett et al. (U.S. Pat. No. 4,788,979); and, T. Nakamura et al., "Surgical Application of Biodegradable Films Prepared from Lactide-Epsilon-Caprolactone Copolymers, Advanced Biomaterials, 7 (Biomater. Clin. Appl.) pp. 759–64 (1987), which disclosures are incorporated herein by reference. Applicants believe any co-polymers of polylactide may be produced from the process disclosed herein.

Fluid transfer mechanisms disclosed throughout this detailed description would normally be a pump. However, Applicants recognize that through design choices other mechanisms for transfer, such as gravitational flow, may also be utilized.

Applicants further recognize that the preferred overall system described herein is a complex combination of many known chemical engineering unit operations. So that the benefit of the overall combination may be recognized, Applicants herein disclose in further detail the selection, operation, and benefits of selecting such unit operations, along with actual laboratory experimental results exemplifying the disclosed advantages.

As previously stated, the crude lactic acids fed to this process (2) may be made up of L-lactic acid or D-lactic acid, or combinations thereof. The composition of the feed, however, does not translate directly through the entire process to define the composition of the polymer product leaving the polymerization reactor (110) through line (108). Applicants recognize that racemization, or conversion of one optical enantiomer to the other, may occur. It is believed that such racemization is driven by such factors as temperature, pressure, time at a given temperature or pressure, the presence of catalysts or impurities, and relative concentrations of the two enantiomers at any given time. The degree of racemization is defined herein by the percent conversion of the optical enantiomer that is present in excess of 50%. As an equation, this calculation would be defined as:

$$\text{degree of racemization (\%)} = 100 - \left( \frac{\% \text{ of majority enantiomer} - 50}{50} \times 100 \right)$$

Thus, an initial composition of 75% L and 25% D which results after racemization to a 50% L, 50% D mixture would equate to a degree of racemization of 100%. In all instances, no matter what initial composition, a 100% degree of racemization coincides with a composition of 50% each enantiomer, or optical inactivity. This recognizes the tendency toward equilibrium at a 50% concentration of each enantiomer, corresponding to optical inactivity. In the most preferred embodiment of the system, each unit operation is controlled to a degree that allows production of a purified lactide mixture with selected chemical and optical composition. The optical composition of the lactide mixture is determined by the relative abundance of D- and L-lactic acid sub-units in the polylactic acid within the lactide reactor. As recognized by Nieuwenhuis et al. in U.S. Pat. No. 5,053,485, the disclosure of which is incorporated herein by reference, the blend of lactide isomers used to produce the polymer affects the physical properties of the polymer, including the biodegradability.

In a preferred embodiment, the evaporator (22) is operated to minimize residence time so that there is little or no effect on optical purity. The prepolymer reactor (38) is also operated to minimize racemization. This includes reducing the residence time within the reactor.

The crude lactide produced in the lactide reactor (60) will be a mixture of the three possible lactides which may be generated from L- and D-lactic acid. These include L-lactide, D-lactide, and meso-lactide.

Applicants have discovered, and detailed in Example 8, that the quality of the crude lactide charged to the distillation system has a significant effect on the operation of said system. In particular, acidic impurities such as lactic acid and low molecular weight oligomers, which are formed by ring opening reactions of lactic acid or water with lactide, can cause premature polymerization in the distillation system. In a preferred embodiment, applicants believe such side reactions may be controlled by partially condensing the crude vapor prior to feeding to distillation to remove impurities.

The distillation system (80) may also be operated to control racemization of the lactide and other side reactions. In a preferred embodiment, this system is designed to minimize racemization by utilizing a packed column distillation system which minimizes liquid holdup, along with a thermal-siphon reboiler which limits residence time of the bottom liquids, and utilizing a minimum reflux ratio to further reduce holdup time in the column. It is, however, recognized that other distillation systems may be utilized with varying impact on the optical purity of the purified lactide and resultant polymer product.

In a preferred embodiment, the distillation system (80) is utilized as a purification step for the lactide so that crystallization of the crude lactide is unnecessary in order to produce a lactide product of suitable purity for polymerization. The lactide reactor (60) is also designed in a preferred embodiment, maximizing surface area between liquid and vapor so that liquid lactide can more easily vaporize. This allows for rapid removal of the generated lactide, which in turn further drives the reaction. Furthermore, as recognized by DeVries in U.S. Pat. No. 4,797,468, which is incorporated herein by reference, a system which utilizes purification steps other than crystallization increases yield. The use of distillation as a purification step also prevents the need to handle solids with the problems with equipment and contamination inherent in such operations.

Applicants have found that utilizing an ester of lactic acid, whether alone or in a hydroxylic medium requires modifications to the overall process to accommodate such feeds. Thus, in a preferred embodiment when an ester of lactic is utilized as a feed material, a catalyst with acid functionality whether in terms of a true acid which is a source of protons, or a Lewis acid which is a source of positive charge density, is used to facilitate the condensation reaction. The presence of the catalyst with acid functionality renders the crude lactide relatively unstable during purification by distillation. In a preferred embodiment, the decomposition of the lactide during purification is avoided by utilizing an insoluble, solid supported catalyst. Alternatively, a soluble homogenous catalyst may be utilized in forming the crude lactide, however, the crude lactide is then subjected to a flash distillation with the catalyst being removed in the bottoms high-boiling stream.

In all embodiments of the present invention, applicants utilize distillation as the final purification means to produce a polymer grade lactide. Several possible distillation processes are disclosed above. Applicants believe each of these systems could be utilized in an overall process which utilizes lactic acid in an aqueous or hydroxylic medium, an ester of lactic acid, an ester of lactic acid in a hydroxylic medium, mixtures of esters of lactic acid, an ester of lactic acid in mixture with lactic acid or a mixture of esters of lactic acid with lactic acid as the feed material for producing the crude lactide to be distilled. One of skill in the art utilizing principles of system design and operation would thus adjust such variables based on the feed composition and resultant purity required.

The following examples further detail advantages of the system disclosed herein:

EXAMPLE 1

Polymerization Technique

The lactide is a mixture of 80% L- and 20% D,L-lactide, recrystallized to high purity. 40 gm of lactide is charged to a flask with magnetic stirring. A THF (Tetrahydrofuran, Burdick and Jackson, high purity, non-spectro) solution containing L-lactic acid, water, or both is added to the lactide. The flask is lowered into an oil bath at 140–160° C. to melt and mix the monomer. This is held for five minutes after complete melting (about 15 minutes total). A starting sample is pulled for GC and/or water analysis. A catalyst solution of 10 wt. % tin(II) 2-ethylhexanoate (Johnson Mathey Electronics, Tech. Grade) in toluene is added and allowed to react for 1 minute. Five gram samples are then pipetted into silanized and nitrogen flushed 20 ml vials. These are quickly placed into a temperature controlled oil bath. Vials are pulled and frozen at various time intervals up to 4 hours.

The samples are prepared for analysis by breaking the polymer out of the vials and dissolving in THF at room temperature on an orbital shaker (about 1–6 hours for 5 grams of polymer in 125 mls THF). The mixture is then diluted to 1% in THF and analyzed utilizing GPC analysis to determine the molecular weight and percent conversion.

EXAMPLE 2

Figure 3:
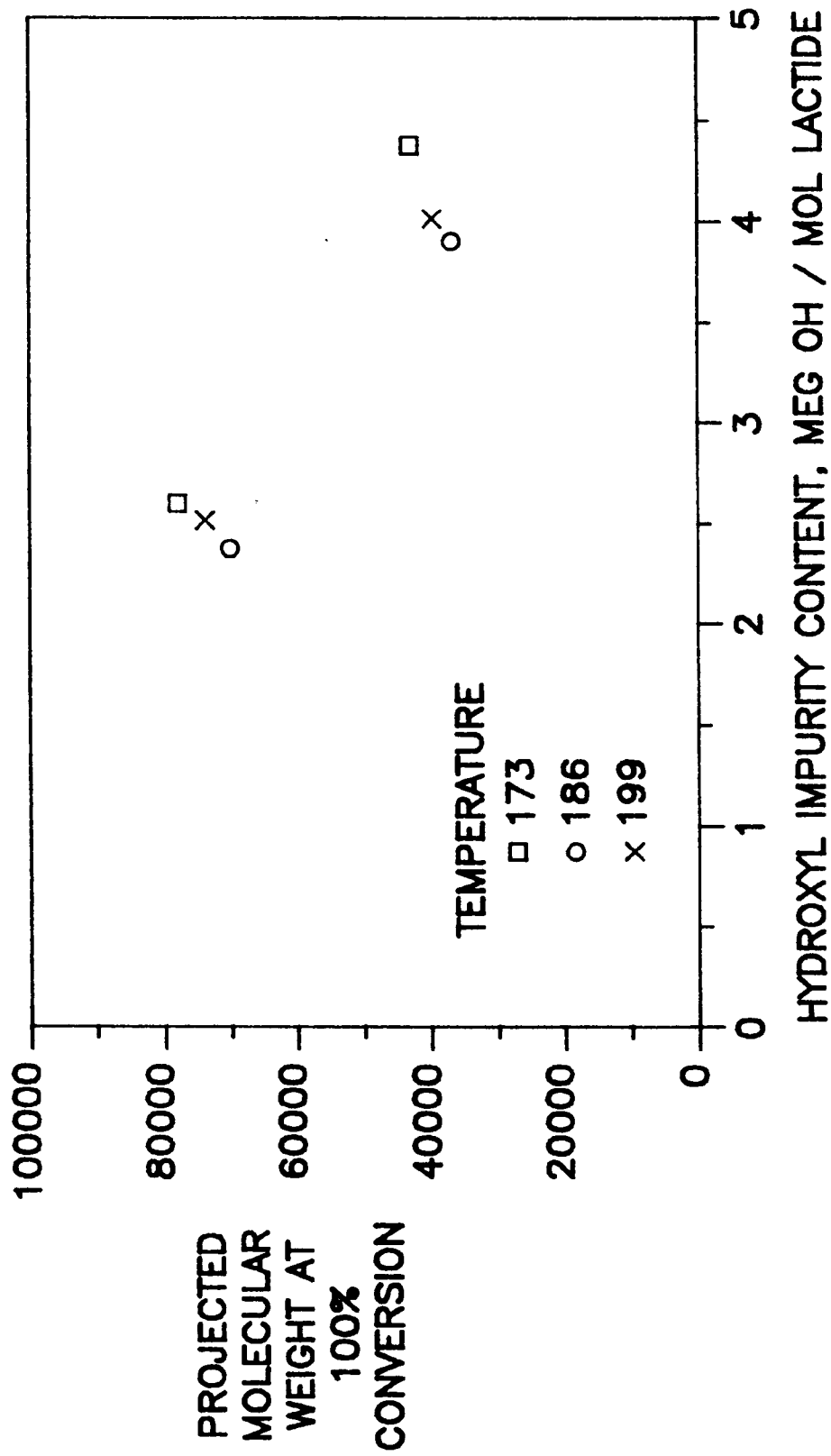
FIG. 3 is a graph showing the effect of hydroxyl impurities on polymer molecular weight at different temperatures.

Polymer Molecular Weight is Controlled by Impurity Level and is Independent of Temperature Experiments were conducted at three different temperatures with two levels of impurities, using the polymerization technique of Example 1. In each case, a projected molecular weight which the polymer would achieve at 100% conversion was determined by GPC analysis of the highest conversion sample and corrected for the unconverted monomer. This method has been shown to give reproducible values and accurately corrects for any effect of sampling at different conversion levels. The results of the experiments are tabulated below and shown graphically in FIG. 3.

| Temperature (° C.) | Hydroxyl impurities meq/mol | Molecular weight, adjusted to 100% conv. |
|---|---|---|
| 173 | 4.45 | 40,100 |
| 173 | 2.52 | 77,500 |
| 186 | 3.90 | 37,800 |
| 186 | 2.38 | 72,100 |
| 199 | 3.98 | 39,400 |
| 199 | 2.48 | 74,900 |

A statistical analysis of variance showed that the molecular weight of the polymer was controlled solely by the level of impurities, with temperature having no effect. Thus, in a preferred embodiment hydroxyl impurities are controlled to desired levels to control the physical properties of the resulting polymer product.

EXAMPLE 3

Figure 4:
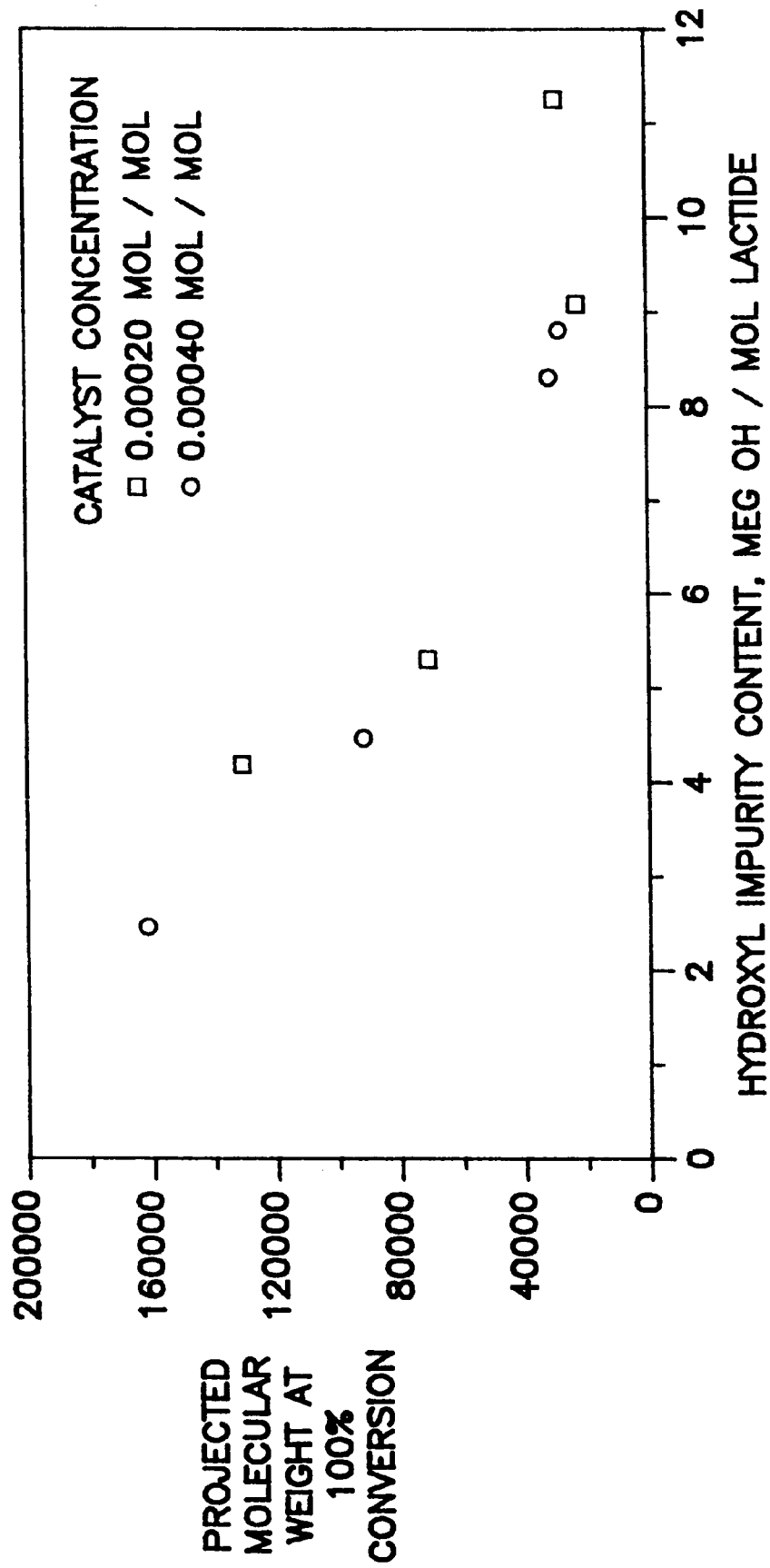
FIG. 4 is a graph showing the effect of hydroxyl impurities on polymer molecular weight at different catalyst concentrations.

Polymer Molecular Weight is Controlled by Impurity Level and is Nearly Independent of Catalyst Concentration The polymers were prepared at 160° C. using the polymerization technique of Example 1. Two levels of water (H=5.9–8.8 meq./mol., L=1.8–3.7 meq./mol.) and two levels of lactic acid (H=0.9–1.3 meq./mol., L=0.1–0.2 meq./mol.) were used in a duplicated factorial design experiment at each of two different levels of catalyst (0.0002 mol/mol; and 0.0004 mol/mol) (eight experiments total). Projected molecular weights were calculated as in Example 2. The results are shown in tabular form below and graphically in FIG. 4.

| Water conc. | Impurity level Lactic acid | Total Hydroxyl Content meq/mol | Molecular weight adjusted to 100% conversion | Catalyst Level |
|---|---|---|---|---|
| L | L | 4.49 | 133,500 | 0.002 |
| H | H | 11.35 | 33,900 | 0.002 |
| L | H | 5.36 | 74,500 | 0.002 |
| H | L | 9.20 | 29,400 | 0.002 |
| L | H | 4.65 | 89,800 | 0.004 |
| H | H | 8.31 | 34,900 | 0.004 |
| L | L | 2.52 | 160,600 | 0.004 |
| H | L | 8.89 | 32,700 | 0.004 |

An analysis of variance revealed that the change in hydroxyl content accounted for 91% of the variance in the molecular weight, while the change in catalyst concentration accounted for only 4% of the variance. Both effects were found to be statistically significant.

These data show, in a preferred embodiment, the critical need to control the level of hydroxyl containing impurities in the lactide in order to control the molecular weight of the final polymer.

EXAMPLE 4

Equilibrium Concentration of Lactide in Polylactic-Acid

Figure 5:
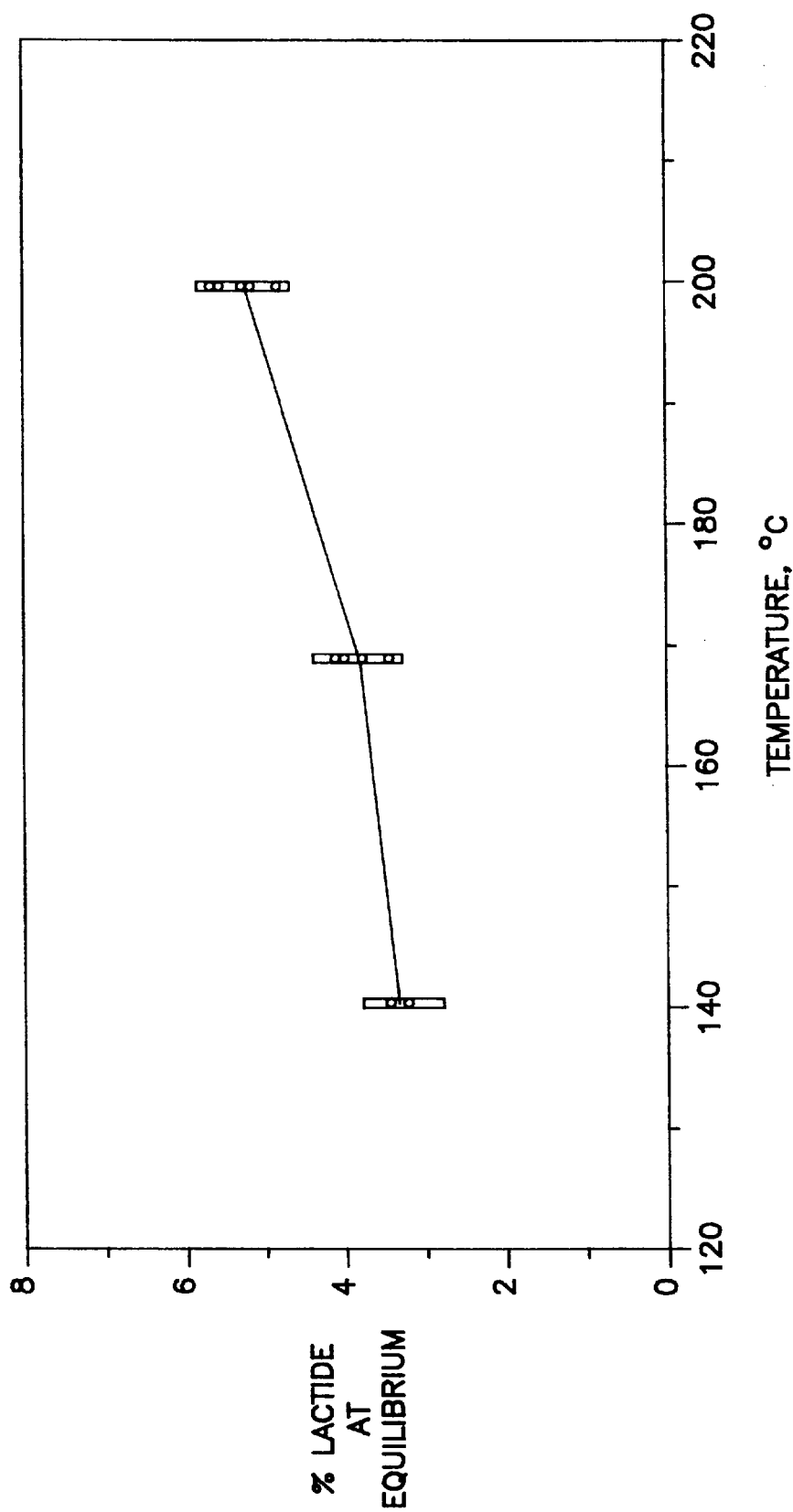
FIG. 5 is a graph showing the equilibrium lactide concentration as a function of temperature.

PLA of 650 MW was heated at atmospheric pressure with either 0.00, 0.05, or 0.15 wt % SnO as a catalyst. The mixtures were held at three different desired temperature for 20 minutes, at which time 10 wt % of purified L-lactide was added to the mixture with stirring. The vessel was fitted with a condenser to prevent the loss of water or other volatile components. Samples were removed from the reaction vessel at times ranging from 5 minutes to 450 minutes and were analyzed using an Ultrastyragel® 100A GPC column (Waters Chromatography, a division of Millipore Corp.) with THF as the mobile phase to determine the concentration of lactide. The concentration data were fit to a simple first order decay model using a non-linear regression software package (SAS Institute, Inc.) to determine the equilibrium values. The resulting projected values for the equilibrium concentrations of lactide are shown in the table below and plotted graphically in FIG. 5. The results show the beneficial effect of rapid removal of lactide from the lactide reactor in preferred embodiments to further drive the lactide generation reaction.

| Temperature (° C.) | Catalyst conc., wt % | Equilibrium lactide, wt % |
|---|---|---|
| 140 | 0.05 | 3.50 |
| 140 | 0.15 | 3.30 |
| 170 | 0.05 | 4.00 |
| 170 | 0.05 | 3.57 |
| 170 | 0.15 | 4.13 |
| 170 | 0.15 | 3.85 |
| 200 | 0.00 | 5.12 |
| 200 | 0.05 | 5.38 |
| 200 | 0.05 | 4.82 |
| 200 | 0.15 | 5.47 |
| 200 | 0.15 | 5.20 |

EXAMPLE 5

Relative Rates of Racemization

Samples of PLA (with and without SnO as catalyst) and lactide were heated and stirred for four hours at 200° C. at atmospheric pressure in a round bottom flask fitted with a condenser to prevent loss of volatile components. The samples were then allowed to cool and the optical purity of the PLA was determined by saponification followed by a measurement of the optical rotation. The lactide sample was analyzed by GC to determine the meso-lactide content, which was then converted to a measurement of optical purity

| | Optical Composition | |
|---|---|---|
| Sample | % L | % D |
| Initial PLA | 96.0 | 4.0 |
| PLA, no catalyst | 95.4 | 4.6 |
| PLA, 0.05 wt % SnO | 87.5 | 12.5 |
| PLA, 0.15 wt % SnO | 90.0 | 10.0 |
| Initial lactide | 99.7 | 0.3 |
| Lactide after heating | 97.2 | 2.8 |

The results of this experiment demonstrate that racemization occurs fastest in PLA which is exposed to catalyst. Thus, in the most preferred embodiment racemization is controlled in the lactide generating reactor. It is however recognized that another area of racemization control will be the evaporators which are used to prepare PLA, because of the long residence times and the possible inclusion of catalyst and catalyzing impurities. In a preferred embodiment the residence time of the lactide in the distillation column will be kept low, minimizing the potential for racemization.

EXAMPLE 6

Effect of Mass Transfer Efficiency on Lactide Composition

Lactide was produced from PLA at several catalyst levels and at two pressures to determine the effect of mass transfer. The catalyst was SnO with constant heat input at a power setting on the Variac of 75%.

The table below shows the effect of changing mass transfer efficiency by adjusting the pressure (vapor phase lactide concentration). Note that the reaction temperatures were similar for each pair of cases.

| Catalyst conc., wt % SnO | 1 mm Hg | | | 10 mm Hg | | |
|---|---|---|---|---|---|---|
| | $T(° C.)$ | meso, wt % | net rate $(hr^{-1})$ | $T(° C.)$ | meso, wt % | net rate $(hr^{-1})$ |
| 0.05 | 213 | 2.6 | 0.79 | 210 | 4.0 | 0.46 |
| 0.50 | 200 | 3.8 | 0.83 | 197 | 5.1 | 0.52 |

The increased mass transfer efficiency at 1 mm Hg vs 10 mm Hg results in significantly higher net lactide production rates and a lower concentration of meso-lactide. In a preferred embodiment the lactide reactor is operated under vacuum to facilitate mass transfer.

The net rate is reported as a reactor turnover rate, based on grams of lactide / (grams of polylactic acid charged * time).

EXAMPLE 7

The Effects of Metal Contaminants Concentrating In the Lactide Reactor

Lactic acid was concentrated and polymerized to form low molecular weight polylactic acid (MW range of about 600–2200) and fed to a continuous pilot scale reactor for the production of lactide. At the end of 1-week of operation a sample of the reactor liquid was taken and analyzed for metals. The results are shown below.

| | |
|---|---|
| Iron | 1200 ppm |
| Chromium | 310 ppm |
| Nickel | 180 ppm |
| Sodium | 89 ppm |
| Calcium | 55 ppm |
| Manganese | 26 ppm |
| Magnesium | 13 ppm |
| Copper | 6 ppm |
| Potassium | ND |

The metals profile clearly shows corrosion of the stainless steel reaction system, either in the formation of the prepolymer or in the lactide generating reactor.

The high metals content, which represents the build-up over a week with no purge on the reactor bottoms, is detrimental to the lactide formation process. The data below demonstrate this effect.

Three lactide runs were made following the usual laboratory process. A control using 650 MW PLA, the control with added iron and chromium (1000 ppm iron from $FeCl_3*6H_2O$, 1000 ppm iron from $FeSO_4*7H_2O$, and 1000 ppm chromium from $CrCl_3*6H_2O$), and the reactor bottoms sample (initial NW 2000). Fresh catalyst, 0.05 wt % SnO, was added to each sample and lactide was generated at 10 mm Hg with a reactor temperature of 230–240° C.

| Sample | Yield | Rate $(hr^{-1})$ | $MW_n$ | $MW_w$ |
|---|---|---|---|---|
| Control PLA | 73% | 0.73 | 3100 | 13300 |
| Control PLA + metals | 63% | 0.90 | 9900 | 126400 |
| Reactor sample | 42% | 0.42 | 6400 | 143400 |

The net rate is reported as a reactor turnover rate, based on grams of lactide / (grams of polylactic acid charged*time). The runs with elevated metals content had lower yield and much higher weight average molecular weight at the end of the reaction, demonstrating the detrimental effects of a high metal content.

It is believed that in a preferred embodiment, a purge of the reactor bottoms will alleviate this problem.

EXAMPLE 8

The Effect of Acidic Impurities on Distillation

Lactide was produced in a continuous pilot plant at rates of 2–5 kg/hr. The starting materials were Purac lactic acid of about 85% concentration. A PLA prepolymer having a range of molecular weights from about 400–2000 MW was made batchwise by heating first at atmospheric pressure and then under vacuum. The prepolymer was used to supply the continuous feed to the lactide reactor. The reactor was run at a temperature of 220–240°C. and pressure of about 35 mm Hg.

Two samples of lactide were distilled in a 2000 ml three-neck flask with mechanical stirring. The lactide was taken overhead through a 2 cm ID by 30 cm glass column with stainless steel packing. Reflux was not controlled, but the column was insulated. The rate of distillation ranged from about 150–370 gms/hr. After taking approximately 80% overhead, the bottoms were analyzed by GC to determine the concentration of oligomers and to calculate the amount of polymerization (based on feed) which had occurred. The table below shows the relationship between the concentration of acidic impurities in the crude lactide and the extent of polymerization during distillation. The data show the effect of acidic impurities on final polymer molecular due to the increased oligomer content in the purified lactide.

| Sample | Acidic Impurity meq [COOH]/mol lactide | Percent of Charge taken overhead | Oligomer Increase as % of feed |
|---|---|---|---|
| #1 | 19 | 92% | 0.5% |
| #2 | 43 | 80% | 7.6% |

EXAMPLE 9

Distillation of Crude Lactide

The overhead fraction from Example 8 was collected in three receivers, containing 14%, 36%, and 28% of the crude lactide charge, respectively. The first fraction contained over 5 wt % lactic acid and was discarded. Fractions 2 and 3 were combined and redistilled, yielding a lactide fraction with total acidic impurities of 4.4 milliequivalents/mol of lactide. This fraction was polymerized using the polymerization technique of Example 1 (temperature 180° C., catalyst/ monomer ratio 1:5000), yielding a polymer with number average molecular weight of 42,100 at 100% conversion and weight average molecular weight of 76,300. Actual conversion was 84.6% at 2 hours.

Applicants have also completed experiments and experimental development to show the overall feasibility and advantages of the disclosed process for production of polylactide beginning with an ester of lactic acid as the feed material. Although, as outlined above, there are many similarities between a polylactide process utilizing lactic acid as a feed source and such process utilizing an ester of lactic acid as the feed material, variations in operating conditions and equipment arrangement along with catalyst usage have been discovered. The following examples, Examples 10–13, document experimental work done by applicants in the area of producing polylactide from the ester of such lactides. Example 10 demonstrates use of a catalyst for completing the condensation reaction from an ester of lactic acid to a polylactide prepolymer. Example 11 demonstrates some purification of reaction products along with polymerization of the lactide. Example 12 demonstrates probable control of polymer molecular weight when utilizing a lactate ester by controlling impurities as was previously shown above when utilizing lactic acid and accompanying impurities. Example 13 demonstrates the use of heterogenous or solid, supported catalysts for the production of lactide from an ester of lactic acid.

Unless otherwise indicated, the following experimental materials and test procedures were utilized in Examples 10–13:

Methyl lactate, ethyl lactate, and butyl lactate were supplied by PURAC America, Inc. under the tradename PURASOLV and used without further purification.

Gas chromatography analysis (GC) for lactate ester oligomers was performed using a Hewlett Packard model 5890 with a DB-17 (J & W Scientific) column. The injector port temperature was 200° C. The column temperature started at 40° C. and was ramped to 250° C. at 10° C./min, then held for 10 minutes. Flame ionization detection (FID) was used. Except where noted, the results of GC analysis to determine composition are based on area percent, uncorrected for percent recovery or relative response factors.

Gel Permeation Chromatography was performed using a Waters Chromatography system with Ultrastyragel® columns. Chloroform (B & J high purity) was used as a solvent. Calibration used polystyrene standards supplied by TSK.

EXAMPLE 10

Catalyzed and Non-Catalyzed Condensation Reactions with Lactic Acid and Ethyl Lactate 2.65 kilograms of lactic acid (heat-stable grade), supplied by PURAC, was heated at atmospheric pressure under a nitrogen atmosphere to a temperature of 180° C. No catalyst was added. 600 grams of overhead, greater than 99% water, was removed during this phase. The material was allowed to cool. Heating was resumed with the flask at a pressure of 50 mm Hg. A slight boil was maintained as the material was heated to 180° C., removing another 135 grams of material. The lactic acid content of the second overhead is estimated to be about 2%, with the remaining material being water. Total heating time for the atmospheric phase was 5.5 hours, and for the vacuum phase was 3.5 hours. The material was a light tan color. Titration of the acid group content showed the material to have an average number average molecular weight of 650 g/mol, corresponding to 9 repeat units. Several samples made following the same procedure were tested and shown to have a lactide concentration of less than 5 weight percent.

250 grams of methyl lactate were heated at atmospheric pressure under a nitrogen atmosphere to a temperature of 145° C. The material boiled at 145° C. No catalyst was added. No condensate was generated during 3 hours of heating and the pot material maintained boiling at 145° C. The pot material was colorless and contained 99% methyl lactate and 1% DP2. No reaction was apparent.

225 grams of ethyl lactate were heated with 3.5% tin(II) ethylhexanoate catalyst at atmospheric pressure under a nitrogen atmosphere to a temperature of 145° C., for 3 hours. The material initially boiled at 140° C., due to the ethanol present. The overhead consisted primarily of ethyl lactate and the expected condensation byproduct ethanol. The pot material was slightly green and contained 46.2% ethyl lactate, 32.3% DP2, 13.3% DP3, 4.1% DP4 and 1.0% D,L-lactide.

EXAMPLE 11

Distillation of Lactide Generated from Methyl Lactate in the Presence of Fascat® 9100 Catalyst 2.2 kilograms of methyl lactate were heated with 0.6% Fascat® 9100 (Atochem North America, Inc.) catalyst at atmospheric pressure under a nitrogen atmosphere to a temperature of 165° C., for 5.0 hours. The material initially boiled at 125° C. The overhead consisted primarily of methyl lactate and the expected condensation byproduct methanol. Total weight of distillate was 350 gms, consisting of 91% methanol. The material was allowed to cool. Heating was resumed with the flask at a pressure of 50 mm Hg. A slight boil was maintained as the material was heated to 145° C., removing another 165 grams of material. The methyl lactate content of the second overhead is estimated to be about 83%, with the remaining material being methanol. Total heating time for the vacuum phase was 6.8 hours.

The material was heated to 200° C. and the pressure reduced to 10 mm Hg. The distillate was partially condensed to form a product fraction and the remaining vapors were further condensed to form an overhead fraction.

Overhead: 67.3% methyl lactate, 16.2% DP2, 1.0% DP3 and 11.7% D,L-lactide. Response factor corrected concentrations were 64% methyl lactate, 15% DP2, 1% DP3 and 10% D,L-lactide.

Product: 3.1% methyl lactate, 6.9% DP2, 1.8% DP3, 0.2% DP4, and 77.6% D,L- and 9.3% meso-lactide. Response value corrected concentrations were 3% methyl lactate, 7% DP2, 2% DP3, 76% D,L-lactide and 9% meso-lactide.

Purification of product material by distillation in a packed column at 10 mm Hg and 150° C. resulted in a fraction containing 0.2% DP2, 8.8% meso and 90.3% D,L-lactide. The purified lactide was polymerized with tin(II) ethylhexanoate (Aldrich Chemicals) at 3000:1 molar ratio and 185° C. for 1.5 hours. Polymerized lactide resulted in a weight and number average molecular weight (Mw and Mn) of 121,500 and 55,000 respectively and a 97.5% lactide conversion.

EXAMPLE 12

Molecular Weight Control of Polylactide Produced From an Ester of Lactic Acid Feed Source Purified lactide (100% L-lactide, supplied by Boehringer Ingelheim KG) was polymerized in a glass vial at 185° C.

for 2 hours and 3000:1 monomer:catalyst molar ratio of tin(II) ethylhexanoate catalyst (Aldrich Chemicals), achieving over 90% conversion to polymer with a number average molecular weight of 116,000. The experiment was repeated with addition of either lactic acid or ethyl lactate as a molecular weight control agent. The results are tabulated below.

| Acid Weight % Control Agent | Source of Control Agent | |
|---|---|---|
| | Ethyl Lactate | Lactic |
| | Polymer Molecular Weight | |
| 0.15 | 83,900 | 57,300 |
| 0.30 | 52,600 | 40,200 |
| 0.50 | 32,600 | 24,800 |
| 1.00 | 19,600 | 13,800 |

The polymers formed with ethyl lactate as the control agent had a molecular weight which averaged 37% higher than the polymers formed with lactic acid as the control agent. This implies that purification requirements to meet a specified molecular weight may be slightly lower for a process based on lactate esters rather than on lactic acid feed, if autogenous impurities are used as the molecular weight control agent.

EXAMPLE 13

2.5 kilograms of methyl lactate were heated with 3.5 wt. % Amberlyst® 36 resin (Rohm and Haas) catalyst at 80 mm Hg, under a nitrogen atmosphere, to a temperature of 104° C., for 10.75 hours. The material initially boiled at 70° C. The overhead consisted primarily of methanol with some methyl lactate, total volume of distillate—505 ml at 81% methanol. The material was allowed to cool, and the catalyst exchanged with fresh Amberlyste® 36 resin at 4.5 wt. %. Heating was resumed with the flask at a pressure of 40 mm Hg. A slight boil was maintained as the material was heated to 115° C., removing another 275 ml of material. The methyl lactate content of the second overhead is estimated to be about 40%, with the remaining material being methanol. Total heating time for this phase was 11.25 hours. The material was allowed to cool, and the catalyst exchanged with fresh Amberlyst® 36 resin at 5.5 wt. %. Heating was resumed with the flask at a pressure of 25 mm Hg. A slight boil was maintained as the material was heated to 115° C., removing another 120 ml of material. The methyl lactate content of the third overhead is estimated to be about 50%, with the remaining material being methanol. Total heating time for this phase was 6 hours. The material was a dark orange color.

The composition of the pot was monitored as a function of time, with the results shown below. These concentrations are calculated upon correction for response factors.

| Initial Charge: 2500 Grams Methyl Lactate | | | | | | |
|---|---|---|---|---|---|---|
| Time (hrs) | Methanol (ml) | Methyl lactate | DP2 | DP3 | DP4 | L-lactide |
| — | 80 | 90.5 | 7.4 | 0.3 | — | 0.1 |
| 6.5 | 264 | 54.2 | 38.5 | 8.6 | 0.5 | 0.9 |
| 9.2 | 411 | 27.4 | 40.2 | 22.7 | 3.5 | 1.9 |
| 13.5 | 485 | 18.6 | 34.0 | 27.0 | 5.5 | 2.0 |
| 15.2 | 511 | 15.3 | 29.4 | 27.3 | 6.5 | 2.1 |
| 20.2 | 574 | 7.3 | 15.5 | 23.0 | 8.5 | 4.8 |
| 20.7 | 584 | 6.4 | 14.2 | 19.0 | 6.8 | 4.3 |
| 27.0 | 656 | 3.2 | 8.2 | 14.0 | 7.6 | |

The results are very similar to those obtained using homogeneous catalysts.

EXAMPLE 14

Example Using a Vertical Wiped Film Evaporator

Lactic acid was condensed to form poly(lactic acid) with molecular weight of 1000 g/mol in a batch reactor, heating first at atmospheric pressure and then under vacuum. No process stabilizer was used. A catalyst, tin(IV) butyltin tris (2-ethylhexanoate), available commercially as FASCAT® 9102, was added to a tin level of 0.5 wt % and 1.0 wt %.

This material was fed to a continuous wiped film evaporator equipped with an internal condenser commercially available as a short-path evaporator from UIC., Inc. in Jolliet, Ill. Crude lactide was distilled across to the condenser as it was formed, and unconverted material flowed out to a bottoms residue receiver. The unit was made of glass and had an evaporator with 0.06 $m^2$ surface area. The feed temperature was set at 150° C., condenser temperature was 100° C., bottoms residue temperature was 215° C., with a wiper speed at 400 rpm.

A number of trials were made at various pressures, feed rates, and evaporator temperatures. The yield of crude lactide was determined from the measured flow rates of the overhead and bottoms products. Product rates are reported both on a unit area basis and on a reactor turnover basis, assuming a film thickness of 0.2 mm (nominal residence time of 2.4 minutes for 300 cc/hr feed). The reactor turnover basis is (mass of lactide per hour) / (reactor mass hold-up). The results of the tests are shown in the table below.

| Catalyst (wt % Sn) | Evap. Temp. (C) | Press. (mm Hg) | Feed Rate (cc/hr) | Crude Lactide Yield (%) | Rate (kg/hr*m) | Rate ($hr^{-1}$) |
|---|---|---|---|---|---|---|
| 0.5 | 230 | 10 | 300 | 27 | 1.9 | 6.7 |
| 0.5 | 250 | 10 | 300 | 41 | 2.7 | 10.2 |
| 1.0 | 230 | 10 | 300 | 43 | 3.1 | 10.7 |
| 1.0 | 250 | 10 | 300 | 78 | 5.8 | 19.5 |
| 1.0 | 250 | 10 | 300 | 93 | 6.0 | 23.2 |
| 1.0 | 250 | 10 | 600 | 45 | 5.6 | 22.5 |
| 1.0 | 250 | 25 | 300 | 59 | 4.0 | 14.7 |

These test results show that the production of lactide at specific rates of more than 10 $hr^{-1}$ using a thin-film technology, are much higher than the typical production rates of less than about 1 $hr^{-1}$.

EXAMPLE 15

Example Using a Horizontal Wiped Film Evaporator

Lactic acid was condensed to form two batches poly (lactic acid) with molecular weights of 610 g/mol, with catalyst to provide a tin content of 0.50 wt %, and 790 g/mol, with catalyst to provide a tin content of 1.0 wt %. The catalyst was tin (IV) butyltin tris(2-ethylhexanoate), available commercially as FASCAT® 9102. No process stabilizer was added.

This material was fed to a continuous horizontal wiped film evaporator, which is commercially available from LCI Corp. in Charlotte, N.C. The evaporator has tapered sides to feed the material through the reactor and to allow adjustment of the rotor clearance. Crude lactide was vaporized as it was produced and condensed to form the crude lactide product. The unit was made of metal and had an evaporator with 0.40 m$^2$ surface area. The feed temperature was maintained at about 170° C., the condenser temperature was 105–120° C., with a wiper speed of about 530 rpm. The clearance between the wall and the rotor was about 1 mm.

A number of trials were made at various pressures, feed rates, and evaporator temperatures. The yield of crude lactide was determined from the measured flow rates of the overhead and bottoms products. Product rates are reported both on a unit area basis and on a reactor turnover basis, assuming a nominal film thickness of 6 mm (nominal residence time of 5 minutes for 75 lb/hr feed). The reactor turnover basis is (mass of lactide per hour) / (reactor mass hold-up). The results of the tests are shown in the table below.

| Catalyst (wt % Sn) | Evap. Temp. (C) | Product Bottoms Temp. (C) | Press. (mm Hg) | Feed Rate (lb/hr) | Crude Lactide Yield (%) | Rate (kg/hr*m$^2$) | Rate (hr$^{-1}$) |
|---|---|---|---|---|---|---|---|
| 0.5 | 229 | 175 | 37 | 42 | 5 | 2 | 0.3 |
| 0.5 | 239 | 177 | 37 | 42 | 19 | 9 | 1.3 |
| 0.5 | 248 | 177 | 36 | 41 | 54 | 25 | 3.5 |
| 0.5 | 248 | 178 | 35 | 41 | 56 | 26 | 3.7 |
| 0.5 | 248 | 176 | 21 | 41 | 80 | 37 | 5.2 |
| 0.5 | 257 | 160 | 20 | 43 | 100 | 49 | 6.9 |
| 0.5 | 258 | 179 | 20 | 73 | 53 | 44 | 6.2 |
| 0.5 | 266 | 178 | 20 | 111 | 51 | 64 | 9.1 |
| 0.5 | 266 | 164 | 20 | 74 | 80 | 67 | 9.4 |
| 0.5 | 266 | 192 | 20 | 91 | 55 | 57 | 8.0 |
| 0.5 | 266 | 164 | 30 | 71 | 66 | 53 | 7.5 |
| 0.5 | 276 | 180 | 30 | 71 | 92 | 74 | 10.4 |
| 1.0 | 259 | 212 | 39 | 66 | 55 | 41 | 5.8 |
| 1.0 | 266 | 224 | 40 | 71 | 73 | 59 | 8.3 |
| 1.0 | 270 | 228 | 39 | 70 | 77 | 61 | 8.6 |
| 1.0 | 278 | 217 | 38 | 75 | 88 | 74 | 10.6 |
| 1.0 | 279 | 230 | 38 | 93 | 74 | 78 | 11.0 |
| 1.0 | 290 | 229 | 38 | 92 | 84 | 88 | 12.4 |
| 1.0 | 289 | 240 | 38 | 113 | 76 | 97 | 13.7 |
| 1.0 | 296 | 238 | 38 | 112 | 82 | 104 | 14.7 |
| 1.0 | 305 | 223 | 38 | 116 | 91 | 120 | 16.9 |
| 1.0 | 301 | 237 | 38 | 129 | 82 | 120 | 16.9 |

These test results show that the production of lactide at specific rates of 5–20 hr$^{-1}$, are much higher than typical production rates of less than about 1 hr$^{-1}$.

EXAMPLE 16

Example Showing Benefit of Mechanically Agitated Film

The effect of agitation on the rate of crude lactide production was measured in two tests where the agitator speed was varied while keeping other conditions constant. In each case, increases in the agitator speed resulted in an increase in crude lactide production.

Vertical wiped film evaporator test:
Evaporator temperature 250° C., pressure 10 mm Hg, catalyst level 1.0 wt %, feed rate 300 cc/hr.
Agitator speed 70 rpm gave crude lactide yield of 35 wt %, for a rate of 8.7 hr$^{-1}$.
Agitator speed 400 rpm gave crude lactide yield of 78 wt %, for a rate of 19.5 hr$^{-1}$.
Horizontal wiped film evaporator test:
Evaporator oil temperature 248° C., pressure 36 mm Hg, catalyst level 0.5 wt %, feed rate 41 lb/hr.
Agitator speed 330 rpm gave crude lactide yield of 41 wt %, for a rate of 2.7 hr$^{-1}$.
Agitator speed 501 rpm gave crude lactide yield of 54 wt %, for a rate of 3.5 hr$^{-1}$.

EXAMPLE 17

Effect of Antioxidant on Optical Composition

Polylactic acid with molecular weight of 600 g/mol to 1600 g/mol was made by batch processing, consisting of heating L-lactic acid (aqueous, 85% lactic acid by weight) first at atmospheric pressure and then at reduced pressure. An antioxidant, Weston PNPG, was added to the lactic acid at two different levels. The polylactic acid was then charged to a hold tank to feed a continuous lactide production pilot plant.

The polylactic acid was charged to a lactide reactor consisting of a vertical section of 42" diameter pipe with a flat bottom, with hot oil circulated below the bottom plate. The reactor was operated at a temperature of 218° C., a pressure of 31 mm Hg, and a liquid inventory of about 14 kg. The feed rate was 4.5 kg/hr of polylactic acid and 12 ml/hr of FASCAT® 9102 catalyst (available from Atochem). A purge of 1.5 kg/hr was maintained, with the remaining 3.0 kg/hr being converted to crude lactide vapor. Additional lactide vapor is generated from an internal recycle stream from the reboiler of a distillation column, described later. The crude lactide vapor was fed to the side of a distillation column (packed column, 6" diameter, about 5' long) and an overhead of 0.8 kg/hr was removed from the first column. The reboiler bottoms of the first column were fed as a liquid to a port on the side of a second column. The feed port was located below the product take-off port. The second column (packed column, 6" diameter, about 5' long) had an overhead take-off of 0.2 kg/hr and a side port for product take-off of 2.0 kg/hr. The product was a substantially purified lactide which is suitable for polymerization. The reboiler bottoms from the second column were recycled directly back to the lactide reactor, with an estimated flow rate of about 5 kg/hr.

Operating at these processing conditions it was found that using a level of antioxidant to give 0.05 wt % in the poly(lactic acid) yielded a lactide containing about 4–8% meso-lactide. When the antioxidant addition rate was decreased to 0.025 wt % (based on poly(lactic acid)) the meso-lactide content increased to 12–19%.

This example shows the potential for optical composition control by adjusting the level of antioxidant.

Examples Related to Clean-up of Purge Stream

EXAMPLE 18

Demonstration of Hydrolysis

Purge material from a continuous lactide reactor, with molecular weight 3500 and containing residues of a tin catalyst, phosphite stabilizer, and metals leached from the reactor, was hydrolyzed with a 22% aqueous lactic acid solution for four hours, at temperatures from 110° C.–140° C. After 4 hours the hydrolysis was complete. A similar treatment with water instead of lactic acid gave a slow and incomplete hydrolysis.

The hydrolysis with lactic acid yielded a solution of about 55% dissolved lactic acid and a precipitate was obtained. The precipitate amounted to 3.4% of the total mass and contained 191 ppm iron, 33 ppm nickel, 388 ppm chromium, and 206 ppm sodium. Tin and phosphorous were not determined, but were estimated to be present at levels of more than 1%, based on a reactor mass balance. The supernatent liquid contained 23 ppm iron, 5 ppm nickel, 2 ppm chromium, 602 ppm tin, 28 ppm phosphorous, and 18 ppm sodium.

The supernatant liquid was treated two times with carbon (Calgon CPG-LF 12×40). The final liquid contained 32 ppm iron, 7 ppm nickel, 4ppm chromium, 244 ppm tin, 23 ppm phosphorous, and 43 ppm sodium. It was heated to 180° C. for 3 hours, turning green and forming a precipitate.

EXAMPLE 19

Use of Ion Exchange

An aqueous solution of 50% lactic acid (prepared using a method similar to Example 18) was treated by ion exchange using a bed of strong acid cation resin (Ambersep 200, hydrogen form). The feed and product analyses after 10 bed volumes are shown below.

|  | Fe (ppm) | Na (ppm) | Cr (ppm) | Sn (ppm) |
| --- | --- | --- | --- | --- |
| Feed | 650 | 40 | 1.7 | 790 |
| Product | 0.4 | 1.6 | 0.0 | 620 |

The product was heated to 180° C. for three hours and remained clear, water white. It is unknown whether the residual tin will provide catalytic activity for the formation of lactide on subsequent use.

It will be understood, however, that even though these numerous characteristics and advantages of the invention have been set forth in the foregoing description, together with details of the structure and function of the invention, the disclosure is illustrative only, and changes may be made in detail, especially in matters of shape, size and arrangement of the parts or in the sequence or the timing of the steps, within the broad principle of the present invention to the full extent indicated by the broad general meaning of the terms in which the appended claims are expressed.

What is claimed is:

1. A process for the continuous conversion of a crude lactic acid feed in a hydroxylic medium to polylactide, said process comprising the steps of:
   a) providing a source of lactic acid in a hydroxylic medium;
   b) concentrating the lactic acid in the hydroxylic medium by evaporating a substantial portion of the hydroxylic medium to form a concentrated lactic acid solution;
   c) polymerizing lactic acid in the concentrated lactic acid solution by further evaporation of the hydroxylic medium to form polylactic acid molecules having a number average molecular weight of less than about 5000;
   d) forming a crude lactide in the presence of catalyst means for catalyzing the depolymerization of the polylactic acid molecules to form lactide molecules; wherein said step of forming a crude lactide includes loading said polylactic acid molecules into a lactide reactor and vaporizing lactide molecules inside said reactor in such a manner that the reactor mean residence time is no greater than about 20 minutes, said lactide reactor containing a pressure less than ambient;
   e) purifying the crude lactide to form a substantially purified lactide by distilling the crude lactide; and
   f) reacting the substantially purified lactide to form polylactide.

2. The process of claim 1 wherein the streams containing recoverable lactide, lactic acid or oligomers and polymers thereof are recycled.

3. The process of claim 1, wherein said step of forming crude lactide includes vaporizing lactide molecules from a film comprising polylactic acid molecules.

4. The process of claim 3, wherein said step of forming crude lactide includes vaporizing lactide molecules inside a falling film evaporator.

5. The process of claim 3, wherein said step of forming crude lactide includes vaporizing lactide molecules inside an agitated thin-film evaporator.

6. The process of claim 3, wherein said step of forming a crude lactide comprises vaporizing lactide molecules inside a reactor in such a manner that the reactor mean residence time is no greater than about 10 minutes.

7. A process for the continuous conversion of a crude lactic acid feed in a hydroxylic medium to a substantially purified lactide, said process comprising the steps of:
   a) providing a source of lactic acid in a hydroxylic medium;
   b) concentrating the lactic acid in the hydroxylic medium by evaporating a substantial portion of the hydroxylic medium to form a concentrated lactic acid solution;
   c) polymerizing lactic acid in the concentrated lactic acid solution by further evaporation of the hydroxylic medium to form polylactic acid molecules having a number average molecular weight of less than about 5000;
   d) forming a crude lactide in the presence of catalyst means for catalyzing the depolymerization of the polylactic acid molecules to form lactide molecules; wherein said step of forming a crude lactide includes loading said polylactic acid molecules into a lactide reactor and vaporizing lactide molecules inside said lactide reactor in such a manner that the reactor mean residence time is no greater than about 20 minutes, said lactide reactor containing a pressure less than ambient; and
   e) purifying the crude lactide to form a substantially purified lactide by distilling the crude lactide.

8. The process of claim 7, wherein said step of forming crude lactide includes vaporizing lactide molecules inside a falling film evaporator.

9. The process of claim 7, wherein said step of forming crude lactide includes vaporizing lactide molecules inside an agitated thin-film evaporator.

10. A process for the continuous conversion of an ester of lactic acid to polylactide, said process comprising the steps of:
   a) providing a source of the ester of lactic acid;
   b) forming a condensation reaction by-product and polylactic acid in the presence of a catalyst for catalyzing the condensation of molecules of the ester of lactic acid to form polylactic acid, wherein the molecules of polylactic acid have a number average molecular weight of less than about 5,000;

c) forming a crude lactide from the polylactic acid molecules in the presence of a catalyst for catalyzing the depolymerization of polylactic acid to form the crude lactide; wherein the crude lactide is formed in a lactide reactor containing a pressure less than ambient in such a manner that the lactide reactor mean residence time is not greater than about 20 minutes;

d) purifying the crude lactide to form a substantially purified lactide by distilling the crude lactide; and e) reacting the substantially purified lactide to form a polylactide.

11. The process of claim 10, wherein the source of the ester of lactic acid is a single ester or a mixture of esters of the general formula:

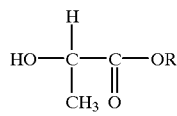

wherein R is a $C_1$–$C_8$ linear or branched alkyl.

12. The process of claim 11, wherein the source of the ester of lactic acid includes a single ester or a mixture of said esters plus lactic acid.

13. The process of claim 10, wherein the forming of polylactic acid in the presence of catalyst means comprises:

(a) providing a catalyst bed reactor system containing a solid supported catalyst means for catalyzing the condensation of molecules of the ester of lactic acid to form polylactic acid molecules; and (b) feeding the ester of lactic acid through said solid supported catalyst means to form said polylactic acid molecules.

14. A process for the continuous conversion of a crude lactic acid feed in a hydroxylic medium to polylactide, said process comprising the steps of:

a) providing a source of lactic acid in a hydroxylic medium;

b) concentrating the lactic acid in the hydroxylic medium by evaporating a substantial portion of the hydroxylic medium to form a concentrated lactic acid solution;

c) polymerizing lactic acid in the concentrated lactic acid solution by further evaporation of the hydroxylic medium to form polylactic acid molecules having a number average molecular weight of less than about 5000;

d) forming a crude lactide in the presence of catalyst means for catalyzing the depolymerization of the polylactic acid molecules to form lactide molecules; wherein said step of forming a crude lactide includes loading said polylactic acid molecules into a lactide reactor and vaporizing lactide molecules inside said lactide reactor, said lactide reactor containing a pressure less than ambient, and said lactide reactor comprising a falling film evaporator or an agitated thin-film evaporator;

e) purifying the crude lactide to form a substantially purified lactide by distilling the crude lactide; and f) reacting the substantially purified lactide of step (e) to form polylactide.

15. A process for preparation of polylactide; said process including the steps of:

a) vaporizing crude lactide from a film of polylactic acid mixture having a number average molecular weight of less than about 5000, in a film generating evaporator, under a pressure less than ambient, to form a crude lactide mixture;

b) distilling the crude lactide mixture to form at least one purified lactide stream; and c) reacting the at least one purified lactide stream to form polylactide.

16. The process according to claim 15 wherein the film generating evaporator is an agitated thin-film evaporator.

17. The process according to claim 15 wherein the film generating evaporator is a falling film evaporator.

* * * * *